(12) United States Patent
Langhals et al.

(10) Patent No.: US 6,491,749 B1
(45) Date of Patent: Dec. 10, 2002

(54) CORE-EXTENDED PERYLENE BISIMIDES

(75) Inventors: Heinz Langhals, Ottobrunn (DE); Susanne Kirner, Sandhausen (DE); Patrick Blanke, Seefeld (DE); Markus Speckbacher, Mettenheim-Hart (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/787,592

(22) PCT Filed: Oct. 11, 1999

(86) PCT No.: PCT/EP99/07614

§ 371 (c)(1),
(2), (4) Date: Mar. 20, 2001

(87) PCT Pub. No.: WO00/23446

PCT Pub. Date: Apr. 27, 2000

(30) Foreign Application Priority Data

Oct. 21, 1998 (DE) .......................... 198 48 555

(51) Int. Cl.$^7$ .................. C09B 5/62; C07D 471/02; C07D 471/12
(52) U.S. Cl. ............... 106/287.21; 546/31; 546/28; 544/233; 544/245; 106/23 R; 106/400; 430/78
(58) Field of Search ............... 546/28, 31; 544/233, 544/245; 430/78; 106/23 R, 287.21, 400

(56) References Cited

U.S. PATENT DOCUMENTS

| | | | |
|---|---|---|---|
| 4,937,164 A | 6/1990 | Duff et al. ............... 430/58 |
| 5,508,137 A | 4/1996 | Langhals ............... 430/78 |
| 5,645,965 A | 7/1997 | Duff et al. ............... 430/59 |
| 6,060,601 A | 5/2000 | Langhals et al. ............... 546/37 |

OTHER PUBLICATIONS

RN 33077–72–4.*
Langhals, H., Chemical Abstracts, 83811 D/46—(EP 039, 085—Apr. 29, 1981).
Langhals, H., Chemical Abstracts, 96:70417x, vol. 96, p. 78 (1982).
Y. Geerts et al., Journal of Materials Chemistry, vol. 8, No. XP–000803180, pp. 2357–2369 (1998).
Y. Nagao et al., Chemistry Letters, XP–000881254, pp. 151–154, (1979).
Y. Nagao et al., Dyes and Pigments, vol. 5, XP–000881349, pp. 171–188, (1984).
H. Langhals, Heterocycles, vol. 40, No. 1, XP–000653314, pp. 477–499 (1995).
H. Kaiser et al., Chem. Ber, vol. 124, XP–002110435, pp. 529–535 (1991).
H. Quante et al., Chem. Mater, vol. 9, XP–000671729, pp. 495–500 (1997).
S. Demmig et al., Chem. Ber., vol. 121, XP–000881317, pp. 225–230 (1988).
T.I. Solomentseva et al., J. Org. Chem.USSR, vol. 22, pp. 943–946 (1986).
M. Zander, Chemiker–Zeitung, vol. 99, No. 2, XP–000872276, pp. 92–93 (1975).
G. Seybold et al., Dyes and Pigment vol. 11, No. 4, XP–000084462, pp. 303–317 (1989).

* cited by examiner

Primary Examiner—Charanjit S. Aulakh
(74) Attorney, Agent, or Firm—David R. Crichton

(57) ABSTRACT

The present inventions relates to nucleus-extended perylenebisimides of formula (I)

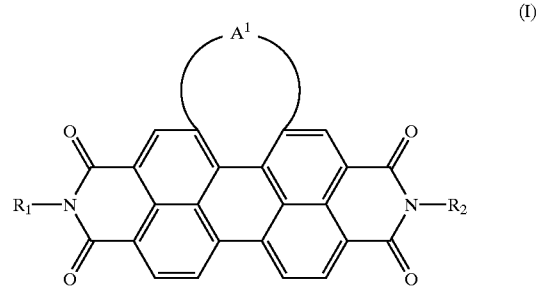

intermediates in the preparation of compounds (I) and processes for the preparation of those intermediates and also processes for the preparation of compounds, (I), and the use thereof as colorants.

7 Claims, No Drawings

CORE-EXTENDED PERYLENE BISIMIDES

This application is a 371 of PCT/EP99/07814 filed Oct. 11, 1999, now WO 00/23446.

The present invention relates to nucleus-extended perylenebisimides of general formulae (I) and (II)

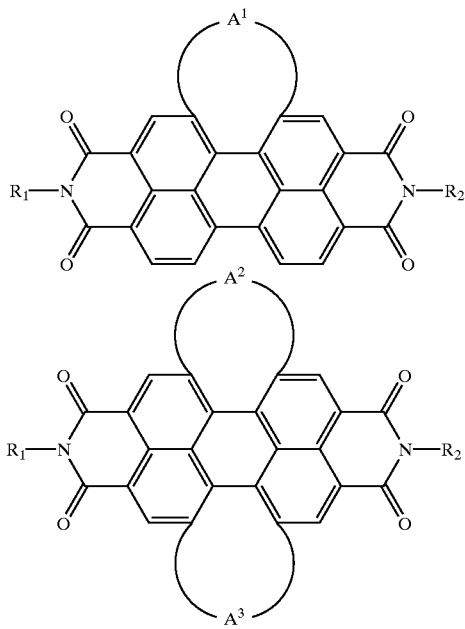

wherein $R^1$ and $R^2$ are each independently of the other unsubstituted or substituted $C_1$–$C_{24}$alkyl, $C_1$–$C_{24}$cycloalkyl, or $C_6$–$C_{10}$aryl, and $A^1$ and $A^3$ are each independently of the other —S—, —S—S—, —CH=CH—, $R^3$OOC—C(—)=C(—)—COOR$^3$, —N=N— or —N(R$^4$)—, or a linkage selected from the group consisting of the organic radicals of formulae (III), (IV), (V), (VI) and (VII)

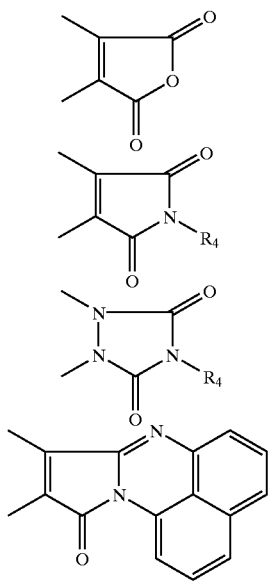

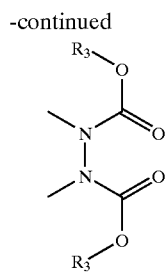

wherein $R^3$ is hydrogen, $C_1$–$C_{24}$alkyl or $C_1$–$C_{24}$cycloalkyl, $R^4$ is unsubstituted or substituted $C_1$–$C_{24}$alkyl, $C_1$–$C_{24}$cycloalkyl, phenyl, benzyl, —CO—$C_1$—$C_4$alkyl, —CO—$C_6H_5$ or $C_1$–$C_4$alkylcarboxylic acid ($C_1$–$C_4$alkyl) ester, and $A^2$ is a linkage of formula (III), (IV) or (V), also to intermediates for the preparation of compounds (I) and (II) and to processes for the preparation of those intermediates and also to processes for the preparation of compounds (I) and (II), and to the use thereof as colourants.

Perylenes, as is known (see Heterocycles, Vol. 40, No. 1, (1995) 477–500), are photostable fluorescent dyes that are often distinguished by high fluorescence quantum yields. A disadvantage thereof is, however, that perylenes have a low degree of solubility in aqueous media.

Chem. Ztg. (1975), 99, 92–93 describes, inter alia, nucleus-extended perylenes that are obtainable by Diels-Alder reaction of 4-phenyl-1,2,4-triazoline-3,5-dione with perylene and that may exhibit absorptions at 600 nm.

Further Diels-Alder reactions on perylenes are described in Heterocycles, Vol. 40, No. 1, 1995. J. Org. Chem. USSR, (1986), 22, 943–946 describes the preparation of thio- and dithio-cyclic derivatives of perylene-3,4,9,10-tetracarboxylic acid. Furthermore, J. Org. Chem. USSR, (1980), 16, 762–7 describes a process for the preparation of nitrogen-cyclic derivatives of perylene-3,4,9,10-tetracarboxylic acid.

The problem underlying the invention was accordingly to provide further nucleus-extended perylenes, especially nucleus-extended perylenebisimides, that preferably as fluorescent dyes have good fastness to heat and to light; perylenes suitable as NIR dyes or as fluorescent markers were also to be provided.

Accordingly, there have been found the nucleus-extended perylenebisimides of general formulae (I) and (II) defined at the beginning.

$C_1$–$C_{24}$Alkyl is, for example, methyl, ethyl, n- or iso-propyl, n-, iso-, sec- or tert-butyl, n- or neo-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, heneicosyl, docosyl or tetracosl, preferably 1-($C_1$–$C_9$alkyl)-$C_2$–$C_{10}$alkyl, such as 1-methyl-ethyl, 1-ethyl-n-propyl, 1-n-propyl-n-butyl, 1-n-butyl-n-pentyl, 1-n-hexyl-1-n-heptyl, 1-n-heptyl-1-n-octyl, 1-n-octyl-1-n-nonyl or 1-n-nonyl-1-n-decyl, or $C_1$–$C_8$alkyl, such as methyl, ethyl, n- or iso-propyl, n-, iso-, sec- or tert-butyl, n- or neo-pentyl, n-hexyl, n-heptyl or n-octyl and especially $C_1$–$C_4$alkyl, such as methyl, ethyl, n- or iso-propyl or n-, iso-, sec- or tert-butyl.

$C_3$–$C_{14}$Cycloalkyl is, for example, cyclopropyl, cyclobutyl, cyclopentyl, cyclohexyl, cycloheptyl, cyclooctyl, cyclononyl, cyclodecyl, cycloundecyl, cyclododecyl, cyclotridecyl or cyclotetradecyl, preferably $C_5$–$C_8$cycloalkyl, such as cyclopentyl, cyclohexyl, cycloheptyl or cyclooctyl.

Especially preferred compounds of formulae (I) and (II) are those wherein $R_1$ and/or $R_2$ denote a secondary alkyl radical, such as 1-($C_1$–$C_9$alkyl)-$C_2$–$C_{10}$alkyl, especially those wherein the radical $R_1$ has a so-called "swallowtail structure", such as 1-methyl-ethyl, 1-ethyl-n-propyl, 1-n-propyl-n-butyl, 1-n-butyl-n-pentyl, 1-n-hexyl-1-heptyl, 1-n-heptyl-1-n-octyl, 1-n-octyl-1-n-nonyl, 1-n-nonyl-1-decyl, or an aromatic radical, especially the phenyl radical, very especially $C_1$–$C_6$alkyl-substituted phenyl, such as 2,6-di-tert-butylphenyl and 2,5-di-tert-butylphenyl.

$C_6$–$C_{10}$Aryl is, for example, phenyl or 1- or 2-naphthyl, especially phenyl.

—CO—$C_1$–C4Alkyl is —CO-methyl, —CO-ethyl, —CO-n-propyl, —CO-isopropyl, or —CO-n-, —CO-iso-, —CO-sec- or —CO-tert-butyl.

$C_1$–$C_4$Alkylcarboxylic acid ($C_1$–$C_4$alkyl) ester is, for example, methylcarboxylic acid methyl ester, methylcarboxylic acid ethyl ester, methylcarboxylic acid n-propyl ester, methylcarboxylic acid isopropyl ester, methylcarboxylic acid n-butyl ester or methylcarboxylic acid isobutyl ester, methylcarboxylic acid sec-butyl ester or methylcarboxylic acid tert-butyl ester or ethylcarboxylic acid methyl ester, ethylcarboxylic acid ethyl ester, ethylcarboxylic acid n-propyl ester, ethylcarboxylic acid isopropyl ester, ethylcarboxylic acid n-butyl ester, ethylcarboxylic acid sec-butyl ester or ethylcarboxylic acid tert-butyl ester, n-propylcarboxylic acid methyl ester or n-butylcarboxylic acid methyl ester.

Hal is, for example, halide and denotes fluoride, chloride, bromide or iodide.

Especially preferred perylene-3,4:9,10-tetracarboxylic acid bisimides of general formulae (I) and (II) are those wherein $R^1$ and $R^2$ are each independently of the other 1-n-hexyl-1-heptyl, 2,5-di-tert-butylphenyl, 1-nonyl-1-decyl or 1-n-butyl-n-pentyl; very especially $R^2$ is $R^1$.

Very special preference is given to perylene-3,4:9,10-tetracarboxylic acid bisimides of general formulae (I) and (II) wherein $A^1$ is —S—, $NR^4$, —CH=CH—, $R^3$OOC—C(-)=C(-)—$COOR^3$, or a linkage of formula (III), (IV), (V), (VI) or (VII) and $A^2$ and $A^3$ are an organic radical of formula (V) or $A^2$ and $A^3$ are each independently of the other an organic radical of formula (III), (IV) or (V).

Preferred perylenes of the present invention are the compounds of formulae (VIII) to (XX) given below, wherein $R^1$ and $R^2$ are especially each independently of the other 1-hexyl-1-heptyl, 2,5-di-tert-butylphenyl, 1-nonyl-1-decyl or 1-butyl-pentyl,

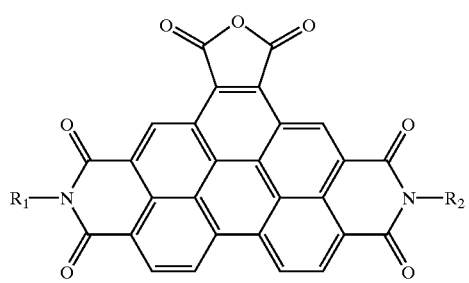

(VIII)

very especially $R^1$ and $R^2$ in (VII) are 1-n-hexyl-1-heptyl, 2,5-di-tert-butylphenyl or 1-butylpentyl, and

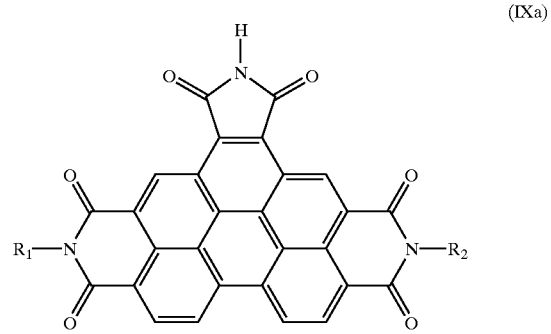

(IXa)

wherein very especially $R^1$ and $R^2$ are 1-n-hexyl-1-heptyl, and

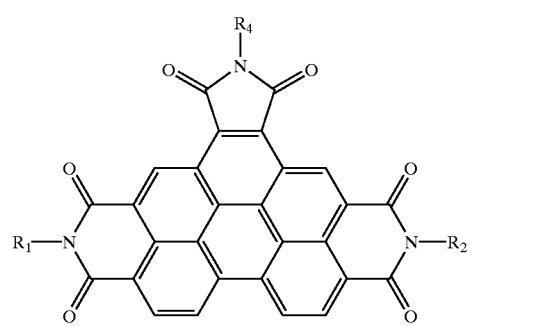

(IXb)

wherein preferably
$R^4$ is unsubstituted or substituted $C_1$–$C_{24}$alkyl, $C_1$–$C_{24}$cycloalkyl, phenyl, and especially cyclohexyl or 2,5-di-tert-butylphenyl, and
$R^1$ and $R^2$ are very especially 1-n-hexyl-1-heptyl, and

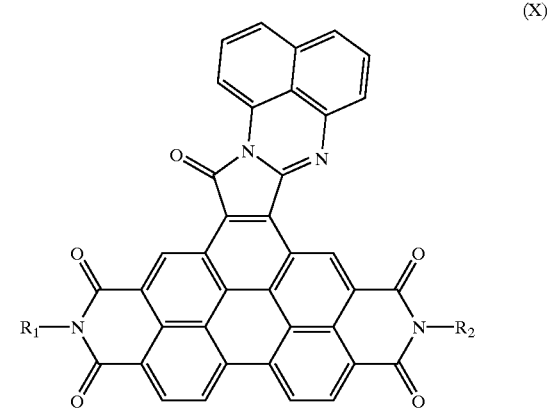

(X)

wherein
R¹ and R² are very especially 1-n-hexyl-1-heptyl, and (XI)

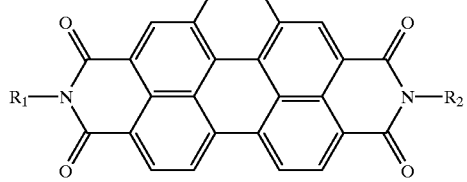

wherein
R¹ and R² are very especially 1-n-hexyl-1-heptyl, and (XII)

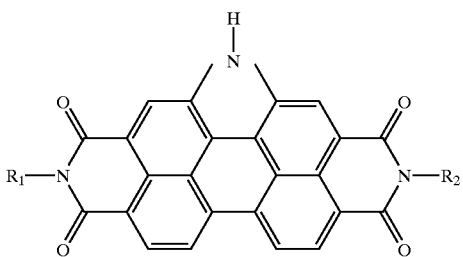

wherein
R¹ and R² are very especially 1-n-hexyl-1-heptyl, 2,5-di-tert-butylphenyl or 1-n-butyl-n-pentyl, and (XIII)

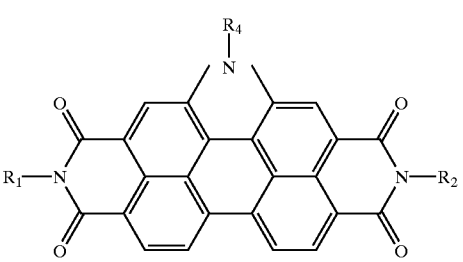

wherein preferably
R⁴ is unsubstituted or substituted $C_1$–$C_{24}$alkyl, phenyl, benzyl, —CO—$C_1$–$C_4$alkyl, —CO—$C_6H_5$ or $C_1$–$C_4$alkylcarboxylic acid ($C_1$–$C_4$alkyl) ester, and especially $C_1$–$C_4$alkyl, more especially methyl, benzyl, —$CH_2COOC_2H_5$, —$COCH_3$ or —CO-phenyl, and
R¹ and R² are very especially 1-n-hexyl-1-heptyl, 2,5-di-tert-butylphenyl or 1-n-butyl-n-pentyl, and (XIV)

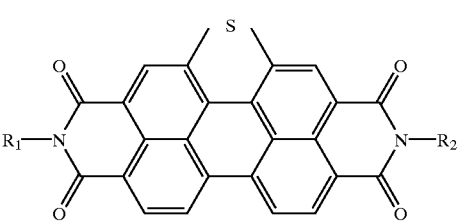

wherein
R¹ and R² are very especially 1-n-hexyl-1-heptyl, 2,5-di-tert-butylphenyl or 1-n-butyl-n-pentyl, and (XV)

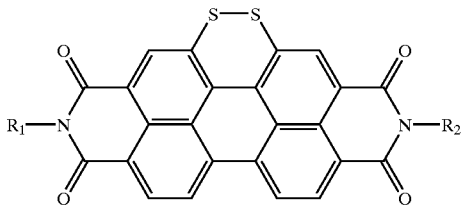

wherein
R¹ and R² are very especially 1-n-hexyl-1-heptyl, 2,5-di-tert-butylphenyl or 1-n-butyl-n-pentyl, and (XVI)

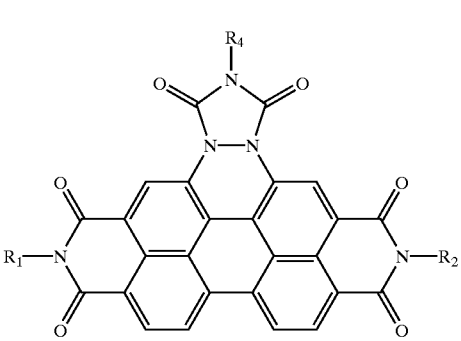

wherein especially
R⁴ is substituted or unsubstituted phenyl, and
R¹ and R² are very especially 1-n-hexyl-1-heptyl, and (XVII)

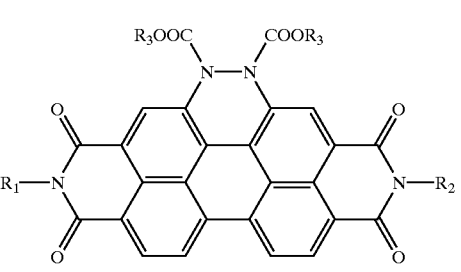

wherein preferably
R³ is $C_1$–$C_4$alkyl, especially methyl or ethyl, and
R¹ and R² are very especially 1-n-hexyl-1-heptyl, and (XVIII)

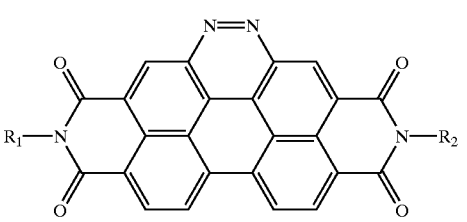

wherein

R$^1$ and R$^2$ are very especially 1-n-hexyl-1-heptyl, and (XIX)

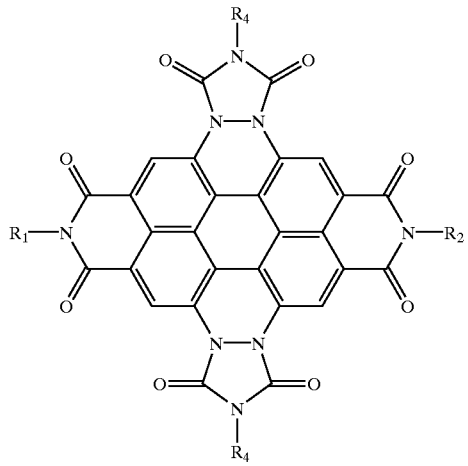

wherein especially

R$^4$ is phenyl, and

R$^1$ and R$^2$ are very especially 1-n-hexyl-1-heptyl, and (XX)

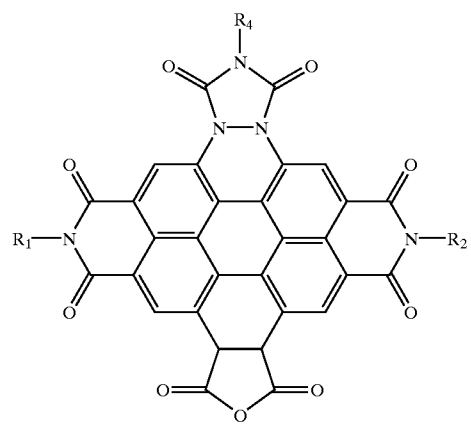

wherein especially

R$^4$ is phenyl, and

R1 and R$^2$ are very especially 1-n-hexyl-1-heptyl.

The perylenebisimides (I) according to the invention wherein A$^1$ is A$^4$, wherein A$^4$ is a linkage selected from the group consisting of the organic radicals of formulae (III), (IV), (V) and (VII), and perylenebisimides (II) wherein A$^2$ is A$^5$, wherein A$^5$ is a linkage of formula (III) or (V), and A$^1$ is A$^6$, wherein A$^6$ is a linkage of formula (V), are preferably obtained by Diels-Alder reactions, as described in J.Chem. Soc. (1957), 96, 5616–4619.

The present invention accordingly relates also to a process for the preparation of perylenebisimides (I) wherein A$^1$ is A$^4$, wherein A$^4$ is a linkage selected from the group consisting of the organic radicals of formulae (III), (IV), (V), (VII) and —N=N—, by Diels-Alder reaction of a diene with a dienophile at elevated temperature, wherein there are reacted, as diene, a perylenebisimide of formula (XXI)

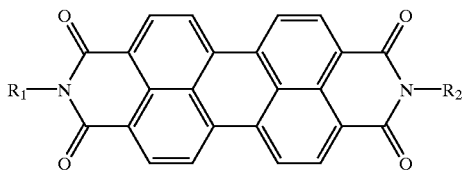

(XXI)

and, as dienophile, a compound selected from the group consisting of the compounds of formulae (XXII), (XXIII) and (XXIV)

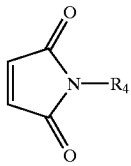

XXII

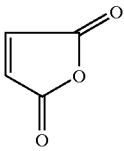

(XXIIa)

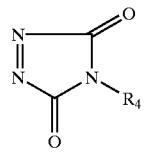

(XXIII)

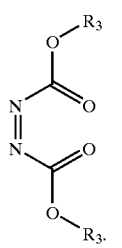

(XXIV)

The order in which the starting materials (XXI) and (XXII), (XXI) and (XXIIa), or (XXI) and (XXIII), or (XXI) and (XXIV), are added is not generally important. It has, however, proved to be advantageous to use a compound of formula (XXII), (XXIIa), (XXIII) or (XXIV) as the initial charge and then to add the compound (XXI).

The compounds of formulae (XXII), (XXIIa), (XXIII) and (XXIV) are generally used in excess, preferably in a molar ratio of compounds (XXII):(XXI), (XXIIa):(XXI), (XXIII):(XXI) or (XXIV):(XXI) in the range of from 1.1:1 to 20:1, especially from 1.3:1 to 15:1.

The reaction is preferably carried out at a reaction temperatures in the range of from 80 to 200° C., especially from 100 to 150° C. According to observations hitherto, the success of the reaction is not dependent upon the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 4 weeks, especially in the range of from one day to 4 weeks.

It has proved advantageous to carry out the reaction in the presence of an organic solvent. As solvent there come into consideration, for example, dipolar aprotic solvents, such as acetonitrile, benzonitrile, N,N'-dimethylformamide, N,N'-dimethylacetamide, nitrobenzene, N-methylpyrrolidone, aliphatic hydrocarbons, which may if desired be halogenated, such as trichloroethane, dichloroethane, trichloromethane or dichloromethane, or cycloalkanes, such as cyclohexane or cycloheptane, or aromatic hydrocarbons or mixtures thereof, such as benzine (as a mixture of different, essentially aliphatic hydrocarbons), or unsubstituted or alkyl-, alkoxy- or halo-substituted benzene, such as toluene, xylene, anisole or chlorobenzene, and also ethers, such as tetrahydrofuran, dioxane or EtOCH$_2$CH$_2$OH (e.g. in the form of Cellosolve® commercially available from Fluka) or glycol ethers, such as ethylene glycol methyl ether, ethylene glycol ethyl ether, diethylene glycol monomethyl ether or diethylene glycol monoethyl ether, or nitrogen-containing solvents, such as pyridine, triethylamine, picoline or quinoline, and keto-group-containing solvents, such as acetone or methyl ethyl ketone. The above-mentioned solvents may also be used in the form of mixtures with one another.

The weight ratio of solvent to the sum of the reactants is customarily in the range of from 0.001 to 20% by weight, preferably from 0.001 to 10% by weight.

In an especially preferred embodiment of the process according to the invention, a compound of formula (XXII), (XXIIa), (XXIII) or (XXIV), preferably of formula (XXII), is reacted with a compound (XXI).

In a further preferred embodiment, the reaction is carried out in a protective gas atmosphere. Preferred protective gases are, for example, nitrogen and the noble gases, such as helium or argon.

It has also proved to be extremely advantageous to carry out the process according to the invention in the presence of an oxidising agent, for example para-chloranil, in order to rearomatise the addition product.

The perylenebisimides of formula (XXI) are known or can be prepared according to known methods as described in Heterocycles (1995), 40, 477–500, for example by reacting a perylenebisanhydride with a primary amine to form a perylenebisimide.

The present invention relates also to a process for the preparation of perylenebisimides (II) wherein A$^2$ is an organic radical of formula (III), (IV) or (V) and A$^1$ is (V), by Diels-Alder reaction of a diene with a dienophile at elevated temperature, wherein a perylenebisimide of formula (XXI) is reacted with a compound of formula (XXII), (XXIIa), (XXIII), or (XXIV), or perylenebisimides of formula (XVI) are reacted with compounds of formula (XXII), (XXIIa) or (XXIII).

The reaction parameters generally correspond to those in the Diels-Alder reaction described above.

The compounds of formulae (XXII), (XXIIa), (XXIII) and (XXIV) are generally used in excess, preferably in a molar ratio of the compounds ((XXII) or (XXIIa) or (XXIII) or XXIV)):((XXI) or (XVI)) in a range of from 2.1:1 to 50:1, especially from 1.3:1 to 15:1.

The order in which the starting materials (XXI), (XXII), (XXIIa), (XXIII) or (XXIV) are added is generally not important. It has, however, proved advantageous to use the compound of formula (XXI) as the initial charge and then to add the compounds (XXII), (XXIIa), (XXIII) or (XXIV).

The perylenebisimides (I) and (II) prepared according to the Diels-Alder reactions according to the invention can be purified and isolated in accordance with customary methods, such as by chromatography, especially column chromatography, or crystallisation, especially extractive recrystallisation (e.g. analogously to the method described in Chem. Ber. 118 (1985) 4641–4645)).

Generally the perylenebisimides (I) and (II) can be used after purification and isolation directly for further reactions.

The present invention accordingly relates also to a process for the preparation of perylenebisimides of formula (IXa), (IXb) or (X), wherein the compound of formula (VII) is reacted with a) NH$_3$ or amidosulfuric acid, or b) a primary amine of formula (XXV) H$_2$N—R$^4$, or c) a primary diamine of formula (XXVI)

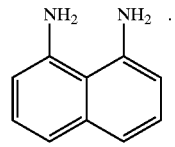

(XXVI)

The amine (XXV) or (XXVI) or NH$_3$ or amidosulfuric acid is generally used in excess, preferably in a molar ratio of the perylenebisimide (I) to (XXV) or (XXVI) or NH$_3$ or amidosulfuric acid in a range of from 1:1.1 to 1:20, especially in the range of from 1:1.3 to 1:15.

The reaction is preferably carried out at reaction temperatures in the range of from 80 to 200° C. According to observations hitherto, the success of the reaction is not dependent upon the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 40 hours, especially in the range of from 2 hours to 25 hours.

It has proved advantageous to carry out the reaction in the presence of an organic solvent. As solvent there come into consideration, for example, those mentioned above. Special preference is given to nitrogen-containing solvents, especially quinoline, and halogenated aliphatic hydrocarbons, such as trichloromethane.

The weight ratio of the sum of the reactants to the solvent is customarily in the range of from 100 to 0.001% by weight, preferably from 50:0.001% by weight.

A preferred embodiment of the process according to the invention relates to the reaction in the presence of N,N'-dicyclohexylcarbodiimide (DCC) in trichloromethane.

An especially preferred embodiment of the process according to the invention relates to the reaction in the presence of N,N'-dicyclohexylcarbodiimide (DCC) and trifluoroacetic acid in trichloromethane.

The molar ratio of DCC to the compound (VII) is customarily in the range of from 20:1 to 1:1, preferably from 15:1 to 1:1 and very especially in the range of from 10:1 to 1:1.

The molar ratio of trifluoroacetic acid to the compound (VIII) is customarily in the range of from 0.0001:100 to 0.1:10.

In a preferred embodiment, the reaction is carried out in a protective gas atmosphere. Preferred protective gases are, for example, nitrogen and the noble gases, such as helium or argon.

It has also been found that the compound (VII) can be converted into a dicarboxylic acid derivative (XXVIIa)

(XXVIIa)

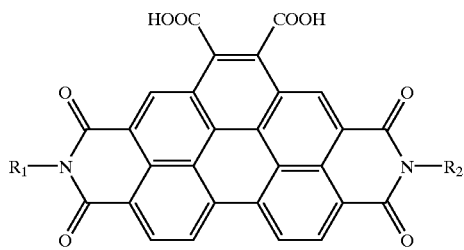

and by esterification into the dicarboxylic acid ester of formula (XXVIIb)

(XXVIIb)

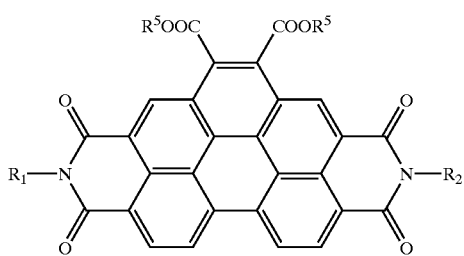

wherein $R^5$ is $C_1$–$C_{24}$alkyl or $C_1$–$C_{24}$cycloalkyl.

A further embodiment of the present invention accordingly relates also to a process for the preparation of compounds of formula (XXVIIa) by hydrolysis of an anhydride, wherein the compound (VIII) is used as anhydride and is reacted with an acid or a base, preferably in an aqueous medium.

The hydrolysis of anhydrides is known and is described, for example, in Survey of Organic Syntheses, by Calvin A. Buehler and Donald E. Pearson, Wiley-Interscience, USA, (1970).

The reaction is preferably carried out at reaction temperatures in the range of from −10 to 200° C., especially from 0 to 150° C. According to observations hitherto, the success of the reaction is not dependent on the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 24 hours.

As acid there may be used, for example, an inorganic acid, such as hydrochloric acid, sulfuric acid, Lewis acids, such as boron trifluoride, or organic acids, such as methanesulfonic acids, formic acid or para-toluenesulfonic acid.

As bases there may be used, for example, alkali metal alcoholates, such as sodium or potassium methanolate or sodium or potassium ethanolate, and alkali metal carbonates and alkali metal hydrogen carbonates, such as sodium carbonate or potassium carbonate, and sodium hydrogen carbonate or potassium hydrogen carbonate, and alkali metal hydroxides, such as sodium hydroxide, potassium hydroxide, especially potassium hydroxide powder (85% by weight potassium hydroxide and 15% by weight water), and also lithium aluminium hydride, potassium tert-butanolate, triethylamine, aluminium alkanolate and also non-nucleophilic bases, such as 1,8-diazabicyclo[5.4.0]undec-7-ene (DBU), 1,5-diazabicyclo[4.3.0]non-5-ene ((DBN) or N,N,N',N'-tetramethylethylenediamine (TMEDA).

The acid or base is generally used in a molar ratio of acid or base to compound (VIII) in the range of from 0.1:1 to 20:1.

It has proved advantageous to carry out the reaction in the presence of an organic solvent. As solvent there come into consideration, for example, those mentioned above.

The weight ratio of the sum of the reactants to the solvent is customarily in the range of from 0.001 to 20% by weight, preferably from 0.001 to 10% by weight.

In a further preferred embodiment, the reaction is carried out in a protective gas atmosphere. Preferred protective gases are, for example, nitrogen and the noble gases, such as helium or argon.

The present invention relates also to a process for the preparation of diester derivatives (XXVIIb) by esterification of a dicarboxylic acid, wherein a compound of formula (XXVIIa) is reacted with an alcohol of formula (XXVIII), HO-$R^5$, or with an alkyl halide of formula (XXIX), Hal-$R^5$, in the presence of an acid or a base.

Suitable bases and acids are those mentioned above.

Methods for the esterification of carboxylic acids are known and described, for example, in Survey of Organic Synthesis, (1970).

A particular embodiment of the process according to the invention relates to the reaction with a base. Non-nucleophilic bases in particular have proved to be advantageous.

Generally the molar ratio of base to compound (XVIIa) is in the range of from 100:1 to 1:100, preferably in the range of from 20:1 to 1:20.

The molar ratio of alkyl halide to base is generally in the range of from 5:1 to 1:5, preferably in the range of from 2:1 to 1:2.

It has proved advantageous to carry out the reaction according to the invention in the presence of solvents. Suitable solvents are those mentioned above.

Generally the solvent is used in an amount sufficient to dissolve the compound (XVIIa).

It has also been found that the dicarboxylic acid derivatives (XVIIa) and anhydrides of formula (VII) can be decarboxylated.

The present invention accordingly relates also to a process for the preparation of perylenebisimides of formula (XI), by decarboxylation of a dicarboxylic acid or an anhydride with copper or a copper-containing compound, wherein a compound of formula (XXVIIa) or (VIII) is reacted in the presence of a solvent.

The decarboxylation of carboxylic acids can, as is known, be carried out with copper in the presence of quinoline (see Survey of Organic Synthesis, (1970), 144, 145 ).

Copper denotes, for example, copper powder, and as copper-containing compound there can be used copper(I) or copper(II) salts, preferably copper(I) or copper(II) oxide, copper chromite or copper sulfate; it is preferred to use copper powder.

Copper or a copper-containing compound is generally used in excess. The molar ratio of copper (or copper equivalent in copper-containing compounds) to the compound of formula (XVIIa) or (VIII) is preferably in the range of from 1.1:1 to 20:1, especially in the range of from 1.3:1 to 15:1.

The reaction is preferably carried out at reaction temperatures in the range of from 80 to 200° C., especially from 120 to 180° C. According to observations hitherto, the success of the reaction is not dependent on the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 48 hours, especially in the range of from 1 hour to 10 hours.

It has proved advantageous to carry out the reaction in the presence of an organic solvent. As solvent there come into consideration, for example, those mentioned above for the process for the preparation of the compound of formula (VII). Especially preferred solvents are nitrogen-containing solvents, with special preference being given to quinoline and 3-picoline.

The weight ratio of the sum of the reactants to the solvent is customarily in the range of from 0.001 to 20% by weight, preferably from 0.001 to 10% by weight.

In a further preferred embodiment, the reaction is carried out in a protective gas atmosphere. Preferred protective gases are, for example, nitrogen and the noble gases, such as helium or argon.

The present invention relates also to perylenebisimides of formula (XXX) and to perylene monoanhydride-monoimides of formula (XXXI)

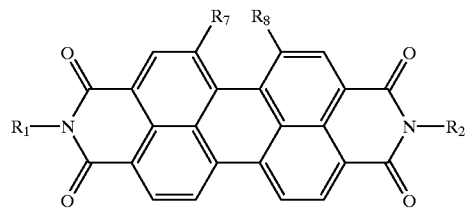
(XXX)

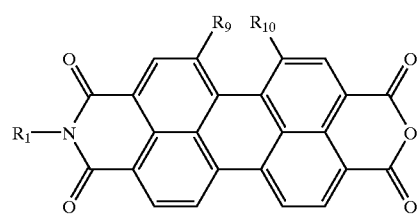
(XXXI)

wherein
$R^7$ and $R^8$ are each independently of the other hydrogen, $NO_2$, $PO(OR^{11})(OR^{12})$, Br, $NH_2$ or $N(R^{11}R^2)_2$, wherein
$R^{11}$ and $R^{12}$ are each independently of the other a radical mentioned under $R^2$, and $R^9$ and $R^{10}$ are each independently of the other hydrogen, $NO_2$, $NH_2$ or $N(R^{11}R^2)_2$.

Special preference is given to substituted perylenebisimides of formulae (XXXII) to (XXXIX), wherein especially $R^1$ and $R^2$ are each independently of the other 1-n-hexyl-1-heptyl, 2,5-di-tert-butylphenyl, 1-nonyl-1-decyl or 1-n-butyl-n-pentyl, (XXXII)
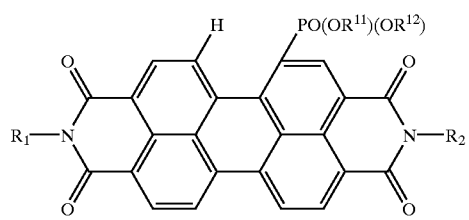

and wherein preferably $R^{12}$ and $R^{11}$ are unsubstituted or substituted $C_1$–$C_4$alkyl, especially methyl or ethyl, and wherein $R^1$ and $R^2$ are very especially 1-hexyl-1-heptyl or 1-butyl-pentyl, and (XXXIII)
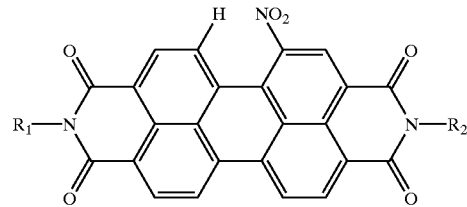

and wherein $R^1$ and $R^2$ are very especially 1-hexyl-1-heptyl, 2,5-di-tert-butylphenyl or 1-butylpentyl, and (XXXIV)
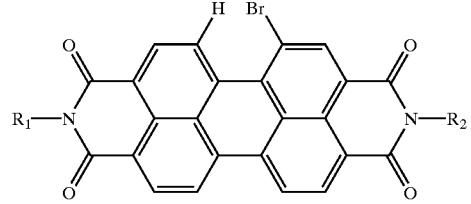

and wherein $R^1$ and $R^2$ are very especially 1-hexyl-1-heptyl, and (XXXV)
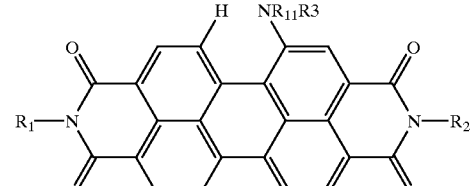

(XXXVa)
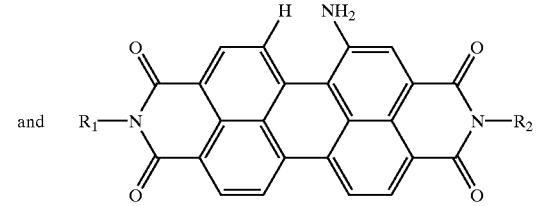

and wherein $R^1$ and R2 are very especially 1-hexyl-1-heptyl or 1-butyl-pentyl, and (XXXVI)
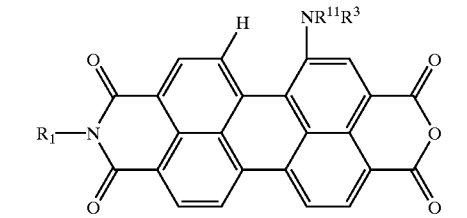

-continued and $R_1-N$ 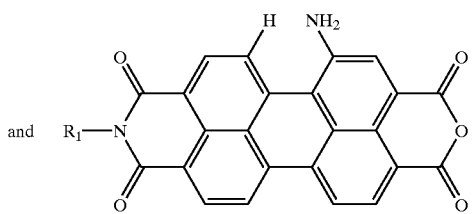  (XXXVIa)

wherein $R^1$ and R 2 are very especially 1-hexyl-1-heptyl or 1-butyl-pentyl, and

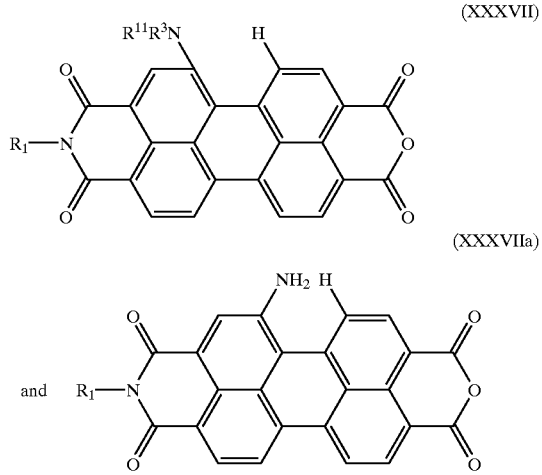

(XXXVII)

(XXXVIIa)

wherein preferably
$R^{11}$ and $R^3$ are unsubstituted or substituted $C_1$–$C_4$alkyl, especially methyl or ethyl, and
wherein $R^1$ is very especially 1-hexyl-1-heptyl or 1-butyl-pentyl, and

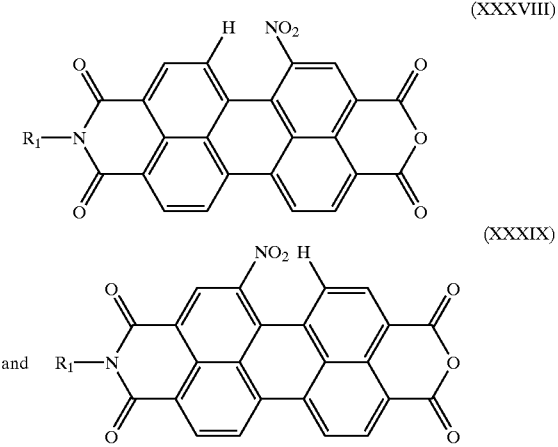

(XXXVIII)

(XXXIX)

wherein $R^1$ is very especially 1-hexyl-1-heptyl or 1-butyl-pentyl.

Perylene monoanhydride-monoimides can be used as starting compounds in the preparation of perylenebisimides in close analogy to known methods. For example, Heterocycles (1995), 40, 477–500 describes how anhydride derivatives of perylenes can be reacted with primary amines to form the corresponding imides.

The anhydride derivatives according to the invention can also be used as fluorescent markers.

The nitro derivatives, especially monosubstituted derivatives, of derivatives of perylenetetracarboxylic acid have hitherto been obtainable only in unsatisfactory yields (see, for example, J. Org. Chem. USSR (Engl. Translation) 1980, 16, 762–766).

It has now been found that perylenebisimides of formula (XXI) and perylene monoanhydride-monoimides of formula (XXXI) wherein $R^9$ and $R^{10}$ are hydrogen can be substituted by a single nitro group in good yields.

The present invention accordingly relates also to a process for the preparation of compounds of formulae (XXXIII), (XXXVIII) and (XXXIX), wherein compounds of formula (XXI) or (XXXI) wherein $R^9$ and $R^{10}$ are hydrogen are reacted with $N_2O_4$ in the presence of a solvent.

The reaction is preferably carried out at reaction temperatures in the range of from –10 to 40° C., especially from 0 to 25° C. According to observations hitherto, the success of the reaction is not dependent on the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 24 hours, especially in the range of from 2 hours to 10 hours.

The molar ratio of $N_2O_4$ to the compounds of formula (XXI) is customarily in the range of from 0.5:1 to 2:1, preferably from 0.8:1 to 1.5:1.

The molar ratio of $N_2O_4$ to the compounds of formula (XXXI) wherein $R^9$ and $R^{10}$ are hydrogen is customarily in the range of from 0.5:1 to 4:1, preferably from 0.8:1 to 1.5:1.

It has proved advantageous to carry out the reaction in the presence of an organic solvent. As solvents there come into consideration, for example, those solvents mentioned above for the process for the preparation of perylenebisimides (I) wherein $A^1$ is $A^4$. Especially preferred solvents are halogenated aliphatic hydrocarbons, such as especially dichloromethane.

A particular embodiment of the process according to the invention relates to the reaction in the presence of a catalyst.

As catalyst there are used, for example, acids, such as sulfonic acids, trifluoroacetic acid, trifluoromethanesulfonic acid, methanesulfonic acid or toluenesulfonic acid, preferably methanesulfonic acid.

The molar ratio of catalyst to the compound of formula (XXI) or (XXXI) wherein $R^9$ and $R^{10}$ are hydrogen is customarily in the range of from 0.0001:1 to 1:1.

The molar ratio of solvent to the compound of formula (XXI) or (XXXI) wherein $R^9$ and $R^{10}$ are hydrogen is generally in the range of from 0.01:1 to 100:1, preferably from 0.1:1 to 50:1.

In a further preferred embodiment, the reaction is carried out in a protective gas atmosphere. Preferred protective gases are, for example, nitrogen and the noble gases, such as helium or argon.

The compounds (XXXIII), (XXXVIII) and (XXXIX) prepared according to the nitration processes according to the invention can be purified and isolated according to customary methods, such as by chromatography, especially column chromatography, or crystallisation, especially extractive recrystallisation.

It has also been found that the nitro derivatives of formulae (XXXIII), (XXXVIII) and (XXXIX) can be converted to their amino derivatives by reduction.

The present invention accordingly relates also to a process for the preparation of compounds of formulae (XXXVa), (XXXVIa) and (XXXVIIa) wherein perylenebisimides of formulae (XXXIII), (XXXVIII) and (XXXIX) are reacted a) with iron in the presence of an acid, or
b) with palladium in the presence of hydride transporters such as triethylamine/formic acid or triethylammonium formate, hydrazine or derivatives thereof, or phosphinic or phosphoric acid.

For example, it is known from Survey of Organic Syntheses, by Calvin A. Buehler and Donald E. Pearson, Wiley-Interscience, USA, (1970), 413 to 417, that nitro compounds can be reduced with iron under acid conditions or with palladium/carbon and hydrogen. Furthermore, reduction with palladium is described, in the presence of formic acid, in J. Chem. Soc. Perkin Trans,I, (1977), 443, and in the presence of triethylammonium formate, in J.Org.Chem.(1977), 42,3491.

The reaction is preferably carried out at reaction temperatures in the range of from −10 to 150° C., especially from 0 to 100° C. According to observations hitherto, the success of the reaction is not dependent upon the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 5 minutes to 24 hours, especially in the range of from 5 minutes to 5 hours, very especially from 5 minutes to 2 hours.

As acid there is customarily used an inorganic or organic acid. Preference is generally given to the use of an inorganic acid, for example hydrochloric acid, especially concentrated hydrochloric acid.

The molar ratio of iron to (XXXIII), (XXXVIII) and (XXXIX) is customarily in the range of from 1:10 to 15:1, preferably from 1:1 to 10:1.

The weight ratio of acid to iron is generally in the range of from 0.001:1 to 100:1.

It has proved advantageous to carry out the reaction in the presence of an organic solvent. As solvent there come into consideration, for example, those listed above for the process for the preparation of perylenebisimides (I) wherein $A^1$ is $A^4$.

The weight ratio of (XXXIII), (XXXVIII) or (XXXIX) to the solvent used is customarily in the range of from 0.001 to 100% by weight, preferably from 0.001 to 20% by weight.

In a preferred embodiment of the process according to the invention, it has proved advantageous to use palladium/carbon instead of palladium.

The weight ratio of palladium/carbon (with 5% by weight palladium based on carbon) to (XXXIII), (XXXVIII) and (XXXIX) is generally in the range of from 0.01:1 to 1:1, preferably in the range of from 0.1:1 to 0.5:1 and very especially in the range of from 0.1:1 to 0.3:1.

The molar ratio of triethylamine to formic acid is customarily in the range of from 1:0.1 to 0.9:1, preferably in the region of 1:0.5 and especially in the region of 1:0.7.

The molar ratio of triethylamine or triethylammonium formate to (XXXIII), (XXXVIII) and (XXXIX) is customarily in the range of from 5:1 to 100:1.

In a further preferred embodiment, the reaction is carried out in a protective gas atmosphere. Preferred protective gases are, for example, nitrogen and the noble gases, such as helium or argon.

The amino derivatives (XLII) and (XLIII) prepared according to the processes of the invention can be purified and isolated in accordance with customary methods, such as by chromatography, especially column chromatography, or crystallisation, especially extractive recrystallisation.

The present invention relates also to a process for the preparation of compounds of formulae (XXXV), (XXXVI) and (XXXVII), wherein the compounds of formula (XXXVa) or (XXXVIa) and (XXXVIIa) are reacted with a base with alkyl halides of formula $R'^{11}$-Hal and/or $R^3$-Hal, wherein Hal is fluoride, chloride, bromide, iodide and $R^{11}$ and $R^3$ are each independently of the other hydrogen or $C_1$–$C_{24}$alkyl, $C_1$–$C_{24}$cycloalkyl, and $R^{11}$ and $R^3$ are preferably the same. Houben-Weyl, Methoden der Organischen Chemie, G. Thieme Verlag Stuttgart, 1957, $4^{th}$ ed., Vol. 11, Pt, 1., Chap. 2 describes methods for alkylating amines.

The reaction is preferably carried out at reaction temperatures in the range of from −10 to 150° C., especially from 0 to 50° C., very especially from 0 to 30° C. According to observations hitherto, the success of the reaction is not dependent on the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 48 hours.

As base there is customarily used an inorganic base, such as, for example, an alkali metal hydroxide, such as potassium hydroxide, sodium hydroxide, or an alkali metal carbonate, such as sodium carbonate, potassium carbonate, or an alkali metal hydrogen carbonate, such as sodium hydrogen carbonate or potassium hydrogen carbonate. It has proved especially advantageous to use aqueous potassium hydroxide. The weight ratio of potassium hydroxide to water is generally in the range of from 0.0001:1 to 1:1.

The molar ratio of the base to the amino derivatives of formula (XXXVa) or (XXXVIa) and (XXXVIIa) is customarily in the range of from 1:10 to 10:1, preferably from 1:5 to 5:1.

The molar ratio of $R^{11}$-Hal to $R^3$-Hal is generally in the range of from 1:100 to 100:1.

It has proved advantageous to carry out the reaction in the presence of an organic solvent. As solvent there come into consideration, for example, those solvents listed above in the process for the preparation of perylenebisimides (I) wherein $A^1$ is $A^4$.

The weight ratio of the sum of the reactants to the solvent is customarily in the range of from 0.001 to 100% by weight, preferably from 0.001 to 20% by weight.

A special development of the present reaction relates to the use of dipolar aprotic solvents.

It has proved especially advantageous to carry out the reaction in the presence of a dipolar aprotic solvent and a phase-transfer catalyst.

As phase-transfer catalyst there may be used, for example, triethylbenzylammonium chloride or triethylbenzylammonium bromide.

The molar ratio of phase-transfer catalyst to (XXXVa) or (XXXVIa) and (XXXVIIa) is customarily in the range of from 0.0001:1 to 0.8:1, preferably from 0.001:1 to 0.5:1.

In a further preferred embodiment, the reaction is carried out in a protective gas atmosphere. Preferred protective gases are, for example, nitrogen and the noble gases, such as helium or argon.

The present invention accordingly relates also to a process for the preparation of compounds of formulae (XXXV) or (XXXVI) and (XXXVII) wherein $R^{11}$ and $R^3$ are alkyl, preferably methyl, wherein the compound of formula (XXXVa) or (XXXVIa) and (XXXVIIa) is reacted with HCHO or with a formaldehyde-providing compound in the presence of formic acid (Leuckart-Wallach reaction) and a solvent, or alkylated with an alkyl iodide and a phase-transfer catalyst, preferably methyl iodide in aqueous potassium hydroxide solution and triethylammonium chloride.

The reaction is preferably carried out at reaction temperatures in the range of from −10 to 200° C. According to observations hitherto, the success of the reaction is not dependent on the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 48 hours.

As formaldehyde-providing compound there may be used, for example, paraformaldehyde or trioxane. Formaldehyde can be used in the form of a gas or in the form of a formalin solution.

The molar ratio of formic acid to the compound of formula (XXXVa) or (XXXVIa) and (XXXVIIa) is customarily in the range of from 1:100 to 100:1.

The concentration of the formalin solution is generally from 35 to 37 per cent by weight.

The molar ratio of the formalin solution to the compounds of formulae (XXXVa) or (XXXVIa) and (XXXVIIa) is customarily in the range of from 1:1 to 100:1.

It has proved advantageous to carry out the reaction in the presence of an organic solvent. As solvent there come into consideration, for example, those solvents listed above for the process for the preparation of perylenebisimides (I) wherein $A^1$ is $A^4$. Particularly advantageous as solvent are N,N'-dimethylformamide, N,N'-dimethylacetamide, nitrobenzene and N-methylpyrrolidone.

The weight ratio of the compounds of formulae (XXXVa) or (XXXVIa) and (XXXVIIa) to the solvent is customarily selected in the range of from 0.001 to 100% by weight, preferably from 0.001 to 20% by weight.

A special development of the present reaction relates to the use of dipolar aprotic solvents.

As phase-transfer catalyst there may be used, for example, triethylbenzylammonium chloride or triethylbenzylammonium bromide.

The molar ratio of phase-transfer catalyst to compounds of formulae (XXXVa) or (XXXVIa) and (XXXVIIa) is customarily in the range of from 0.0001:1 to 0.8:1, preferably from 0.001:1 to 0.5:1.

In a further preferred embodiment, the reaction is carried out in a protective gas atmosphere. Preferred protective gases are, for example, nitrogen and the noble gases, such as helium or argon.

The reaction product is preferably isolated by precipitation with water and subsequent filtration.

It has proved advantageous to adjust the precipitated reaction product in water to a pH value in the range of from 7.5 to 10 with a base.

As base there may be used, for example, sodium hydroxide, potassium hydroxide, sodium carbonate, potassium carbonate, sodium hydrogen carbonate or potassium hydrogen carbonate.

The compounds of formulae (XXXVa) or (XXXVIa) and (XXXVIIa) isolated according to the processes of the invention can be purified in accordance with customary methods, such as by chromatography, especially column chromatography, or crystallisation, especially extractive recrystallisation.

In the present invention it has also been found that trialkylphosphonate derivatives (XXXII) and pyrrolo derivatives (XII) can be obtained from the above nitro derivatives of the compounds of formula (XXXIII) by reaction with trialkyl phosphite.

The present invention accordingly relates also to a process for the preparation of perylenebisimide trialkylphosphonates of formula (XXXII) and perylenebisimide pyrroles of formula (XII), wherein the compound of formula (XXXIII) is reacted with trialkyl phosphite of the formula P(OR$^{12}$)(OR$^{11}$)(OR$^5$) wherein $R^{12}$, $R^{11}$ and $R^5$ are as defined above and are especially $C_1$–$C_4$ alkyl.

Synthesis 1969, 11 to 17, describes methods for the reaction of amines with trialkyl phosphite, so that further details on the subject are superfluous.

The reaction is preferably carried out at reaction temperatures in the range of from −10 to 150° C., especially from 100 to 150° C. According to observations hitherto, the success of the reaction is not dependent on the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 48 hours.

The molar ratio of the nitro derivative (XXXIII) to the trialkyl phosphite is customarily in the range of from 1:1 to 1:500, preferably from 1:10 to 1:200.

It has proved advantageous to carry out the reaction in the presence of an organic solvent. As solvent there come into consideration, for example, those solvents listed above for the process for the preparation of perylenebisimides (I) wherein $A^1$ is $A^4$.

The weight ratio of nitro derivative (XXXIII) to solvent is customarily selected in the range of from 1 to 100% by weight.

In a further preferred embodiment, the reaction is carried out in a protective gas atmosphere. Preferred protective gases are, for example, nitrogen and the noble gases, such as helium or argon.

The pyrrolo and trialkylphosphonate derivatives of formulae (XXXII) and (XII) prepared according to the process of the invention can be purified and isolated in accordance with customary methods, such as by chromatography, especially column chromatography, or crystallisation, especially extractive recrystallisation.

It has proved especially advantageous to separate and purify the pyrrolo and trialkylphosphonate derivatives of formulae (XXXII) and (XII) by column chromatography using trichloromethane as eluant on aluminium oxide.

It has also been found that the pyrrolo derivatives of formula (XII) can be alkylated, benzylated or acylated.

The invention accordingly relates also to a process for the preparation of compounds of formula (XIII), wherein a compound of formula (XII) is reacted with a halide of formula $R^4$-Hal, in the presence of a base.

The reaction is preferably carried out at reaction temperatures in the range of from -10 to 100° C., especially from 0 to 50° C., very especially from 0 to 30° C. According to observations hitherto, the success of the reaction is not dependent on the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 48 hours.

As bases there may be used the bases listed above for the process for the preparation of compounds of formula (XXVII).

The molar ratio of base to pyrrolo derivatives of formula (XII) is customarily in the range of from 1:10 to 10:1, preferably from 1:5 to 5:1.

In a preferred embodiment of the process according to the invention, the reaction of a pyrrolo derivative of formula (XII) with a halide is carried out in the presence of a solvent.

A particular embodiment of the process according to the invention relates to the reaction in the presence of potassium hydroxide powder in the presence of a protic solvent. For example, alcohols, such as methanol, ethanol, propanol, isopropanol, n-, sec- or tert- butanol, n-, sec- or tert-pentanol, have proved to be especially advantageous as protic solvents.

In a further particular embodiment of the process according to the invention, there are used generally non-nucleophilic bases, such as 1,8-diazabicyclo[5.4.0]undec-7-ene (DBU), 1,5-diazabicyclo[4.3.0]non-5-ene ((DBN) or N,N,N',N'-tetramethylethylenediamine (TMEDA).

It has proved advantageous to carry out the reaction in the presence of an organic solvent. As solvent there come into consideration, for example, the solvents listed above for the process for the preparation of perylenebisimides (I) wherein $A^1$ is $A^4$. Special preference is given to N,N'-dimethylformamide, N,N'-dimethylacetamide or N-methylpyrrolidone and to trichloroethane, dichloroethane, trichloromethane or dichloromethane; ethers are especially preferred, with special preference being given to tetrahydrofuran.

The weight ratio of pyrrolo derivative (XII) to solvent is customarily in the range of from 0.001 to 100% by weight, preferably from 0.001 to 20% by weight.

The pyrrolo compound derivatives isolated according to the processes of the invention can be purified in accordance with customary methods, such as by chromatography, especially column chromatography, or crystallisation, especially extractive recrystallisation.

It has also been found in the present invention that the perylenebisimides of formula (XXXIII) are suitable for the nucleus-extension of perylenebisimides with sulfur.

The present invention accordingly relates also to a process for the preparation of compounds of formulae (XIV) and (XV), wherein 1-nitro-perylenebisimides of formula (XXXIII) are reacted with sulfur in the presence of a solvent.

The reaction is preferably carried out at reaction temperatures in the range of from −10 to 200° C., especially from 0 to 150° C. According to observations hitherto, the success of the reaction is not dependent on the pressure range selected. For simplicity's sake, the reaction is customarily carried out at atmospheric pressure, but it is also possible to select pressures in the range of from 10 kPa to 10 MPa. The reaction times are selected, depending on the reaction temperature chosen, preferably in the range of from 1 hour to 40 hours, especially in the range of from 5 hours to 24 hours.

It has proved advantageous to carry out the reaction in the presence of an organic solvent. As solvent there come into consideration, for example, the solvents listed above for the process for the preparation of perylenebisimides (I) wherein $A^1$ is $A^4$. Special preference is given to dipolar aprotic solvents, such as N,N'-dimethylformamide, N,N'-dimethylacetamide, nitrobenzene and N-methylpyrrolidone.

The weight ratio of solvent to the 1-nitroperylenebisimide of formula (XXXIII) is customarily in the range of from 1:1 to 1000:1, preferably from 1:10 to 500:1.

The molar ratio of sulfur to the 1-nitroperylenebisimide (XXXIII) is customarily in the range of from 10:0.1 to 0.9:1, preferably in the range of from 5:0.1 to 4:1.

In a further preferred embodiment, the reaction is carried out in a protective gas atmosphere. Preferred protective gases are, for example, nitrogen and the noble gases, such as helium or argon.

It has proved advantageous to treat the reaction mixture with dilute mineral acid, such as hydrochloric acid, at a temperature in the range of from 80 to 120° C., especially from 90 to 110° C., the desired product being precipitated.

If desired, the resulting precipitate can be washed with water and, if desired, the precipitate can be dried.

Furthermore, the precipitate, which may or may not have been dried, can be purified in accordance with customary methods, such as by chromatography, especially column chromatography, or crystallisation, especially extractive recrystallisation.

A further embodiment of the present invention relates to the use of the perylenes (I), (II), (XXX) and (XXXI) according to the invention as colourants, especially as pigments and dyes, in each case in accordance with methods generally known per se, preferably (a) for melt colouration of polymers, it being possible to use as polymers polyvinyl chloride, cellulose acetate, polycarbonate, polyamide, polyurethane, polyimide, polybenzimidazole, melamine resin, silicone, polyester, polyether, polystyrene, polymethyl methacrylate, polyethylene, polypropylene, polyvinyl acetate, polyacrylonitrile, polybutadiene, polychlorobutadiene or polyisoprene, and the copolymers of the mentioned monomers;

(b) as vat dyes or mordant dyes, for example for dyeing natural materials and, especially, paper, wood, straw, leather, animal skins or natural fibre materials, such as cotton, wool, silk, jute, sisal, hemp, flax or animal hair (e.g. horsehair) and their conversion products, such as viscose fibres, nitrocellulose silk or copper rayon, preferred salts for mordanting being aluminium, chromium and iron salts;

(c) in the manufacture of paints, lacquers, especially automotive lacquers, coating compositions, paper dyes, printing inks, inks, especially for use in ink-jet printers, preferably in homogeneous solution as fluorescent inks, and for drawing and writing purposes, and in electrophotography, for example for dry-copying systems (Xerox process) and laser printers;

(d) for security-marking purposes, such as for cheques, cheque cards, bank notes, coupons, documents, identity papers and the like, where a particular, unmistakable colour impression is to be achieved;

(e) as an additive to colourants, such as pigments and dyes, in which a particular shade of colour is to be achieved; especially luminescent shades are preferred;

(f) for labelling objects for the purpose of mechanically recognising those objects by means of fluorescence, preference being given to the mechanical recognition of objects for sorting, for example for the recycling of plastics, with alpha-numerical printing or bar codes preferably being used;

(g) for frequency conversion of light, for example in order to make longer-wavelength, visible light from short-wavelength light, or for frequency doubling or frequency tripling of laser light in non-linear optics;

(h) for the production of passive display elements for a wide variety of display, information and labelling purposes, for example passive display elements, road signs and traffic signals, such as traffic lights;

(i) as starting material for supraconducting organic materials (via π-π interactions, after doping with, for example, iodine there is usually obtained an intermediate charge delocalisation);

(j) for fluorescent labelling of solids;

(k) for decorative and artistic purposes;
(l) for tracer purposes, for example in biochemistry, medicine, technology and natural science, it being possible to link the colourants according to the invention covalently to substrates or via secondary valences, such as hydrogen bonds or hydrophobic interactions (adsorption); examples thereof are protein-dye combinations, antibody-dye combinations or DNA- or RNA-dye combinations,
(m) as fluorescent dyes in highly sensitive detection methods (see C. Aubert, J. Fünfschilling, 1. Zschokke-Gränacher and H. Langhals, Z. Analyt. Chem. 1985, 320, 361), especially as fluorescent dyes in scintillators;
(n) as dyes or fluorescent dyes in optical light-collecting systems, in fluorescent quantum counters, in fluorescent solar collectors (see H. Langhals, Nachr. Chem. Tech. Lab. 1980, 28, 716), in fluorescence-activated displays (see W. Greubel and G. Baur, Elektronik 1977, 26, 6), in cold-light sources for light-induced polymerisation in the preparation of plastics, for materials' testing, for example in the manufacture of semiconductor circuitry, for the investigation of microstructures of integrated semiconductor components, in photoconductors, in photographic processes, in display, illumination or image-converting systems in which excitation is effected by means of electrons, ions or UV radiation, for example in fluorescent displays, Braun tubes or in fluorescent tubes, as part of an integrated semiconductor circuit, which contain dyes as such or in conjunction with other semiconductors, for example in the form of an epitaxy, in chemiluminescent systems, for example in chemiluminescent light rods, in luminescent immunoassays or other luminescent detection methods, as highlighter inks, especially for lending visual prominence to text and drawings or other graphic products, for identifying signs and other objects where a particular visual colour impression is to be achieved, in dye lasers, preferably as fluorescent dyes for producing laser beams and as Q-switches;
(o) as rheology improvers and
(p) for modifying inorganic solids, such as aluminium oxide, silicon oxide, for example, in zeolite cages, titanium dioxide, tin oxide, magnesium oxide ("xylolith"), silicates, clay minerals, chalk-, gypsum- or cement-containing surfaces such as paints or plaster surfaces in which the free carboxyl function provides special adhesion to the surface, or
(q) as NIR dyes for information technologies.

In particular, the compounds wherein $R_1$ and/or $R_2$ is/are 1-butyl-pentyl, 1-hexyl-1-heptyl, 1-heptyl-1-octyl, 1-octyl-1-nonyl, 1-nonyl-1-decyl and 2,5-di-tert-butylphenyl are distinguished by their good solubility.

EXAMPLES

Example 1a

1-Nitro-N, N'-bis(1-butylpentyl)perylene-3,4:9,10-bis(dicarboximide) (XL)

N,N'-Bis(1-butylpentyl)perylene-3,4:9,10-bis(dicarboximide) (prepared as described in Chem. Ber. 1988, 121, 225–230) 2.00 g (3.12 mmol), 30 ml of dichloromethane, a solution of $N_2O_4$ in dichloromethane, 37 ml (0.085 molar, 3.15 mmol, prepared as described below) and methanesulfonic acid, 0.02 ml (0.30 mmol), are reacted at 25° C. for 6 hours. The reaction mixture is concentrated to about 2 ml. The residue is taken up in 10 ml of toluene and worked up by chromatography on silica gel/toluene. Yield 2.1 g (98%) (XL) in the form of a dark-red powder, m.p. 304° C., $R_f$ (silica gel/toluene): 0.31.

Example 1b

1-Nitro-N,N'-bis(1-hexylheptyl)perylene-3,4:9,10-bis(dicarboximide) (XLI)

N,N'-Bis(1-hexylheptyl)perylene-3,4:9,10-bis(dicarboximide) (prepared as described in Chem. Ber. 1988, 121, 225–230), 2.07 g (2.75 mmol), a solution of $N_2O_4$ in dichloromethane, 14.0 ml (0.198 molar, 2.77 mmol $N_2O_4$/ prepared as described below), and methanesulfonic acid, 0.05 ml (0.77 mmol), are reacted at 25° C. for 7 hours. The reaction mixture is concentrated to about 2 ml. The residue is taken up in 10 ml of toluene and worked up by chromatography on silica gel/toluene. Yield 2.04 g (93%) (XLI) dark-red powder, m.p. 121° C., $R_f$ (silica gel/trichloromethane): 0.84. - $R_f$ (silica gel/toluene): 0.63.

Example 1c

1-Nitro-N, N'-bis(2,5-di-tert-butylphenyl)perylene-3, 4:9,10-bis(dicarboximide) (XLII)

N,N'-bis(2,5-di-tert-butylphenyl)perylene-3,4:9,10-bis(dicarboximide) (prepared as described in Chem. Ber. 1985, 118, 4641–4645), 800 mg (1.04 mmol), dichloromethane, 30 ml, a solution of $N_2O_4$ in dichloromethane, 21 ml (0.05 molar,1.05 mmol, prepared as described below), and methanesulfonic acid, 0.05 ml (0.77 mmol), are reacted at 25° C. for 4 hours. The crude product is concentrated to about 1 ml. The residue is taken up in 10 ml of trichloromethane and worked up by chromatography on silica gel/trichloromethane. Yield: 800 mg (94%)(XLII) dark-red crystalline powder, m.p.>300° C., $R_f$ (silica gel/trichloromethane): 0.45.

Example 1d

1-Nitro-N-(1-hexylheptyl)-perylene-3,4:9,10-tetracarboxylic acid 3,4-anhydride-9, 10-imide (XLIII) and 12-nitro-N-(1-hexylheptyl)-perylene-3, 4:9,10-tetracarboxylic acid 3,4-anhydride-9, 10-imide (XLIV)

N-(1-Hexylheptyl)-perylene-3,4:9,10-tetracarboxylic acid 3,4-anhydride-9, 10-imide, 100 mg (0.175 mmol) (prepared as described in Chem. Ber. 124, 529–535), dichloromethane, 50 ml, a solution of $N_2O_4$ in dichloromethane 5.5 ml (0.03 molar, 0.165 mmol, prepared as described below), and methanesulfonic acid, 0.05 ml (0.77 mmol), are reacted at 25° C. for 4 hours. The crude product is concentrated to about 1 ml. The residue is taken up in 20 ml of trichloromethane and worked up by chromatography on silica gel/trichloromethane/7% glacial acetic acid. Yield: 83 mg (77%) of a mixture of (XLIII) and (XLIV) in the form of a dark-red powder, m.p.: 189–191° C., $R_f$ (silica gel/ dichloromethane /2% glacial acetic acid): 0.73.

Preparation of an $N_2O_4$ solution: $Pb(NO_3)_2$ is heated for a few minutes at from 250 to 600° C. and the $N_2O_4$ gas that is released is introduced into dichloromethane until saturated. To determine the concentration of the solution of $N_2O_4$ in dichloromethane, 10 ml of the solution are shaken together with 10 ml of 30% by weight hydrogen peroxide until the light-brown colour disappears. The result is a two-phase mixture. The lower dichloromethane phase is separated off. The upper aqueous phase is titrated against NaOH (0.1N) using phenolphthalein as indicator to determine the nitric acid content.

Example 2a

N,N'-Bis(1-hexylheptyl)perylene-3,4:9,10-bis(dicarboximide)-1-diethylphosphonate (XLV) and N,N'-bis(1-hexylheptyl)pyrrolo[2,3,4,5-hik]perylene-3,4:8,9-bis(dicarboximide) (XLVI)

(XLI), prepared analogously to Example 1b, 150 mg (0.188 mmol) and triethyl phosphite, 5 ml (29.1mmol), are reacted under an argon atmosphere at 130° C. for 5 hours. The reaction mixture is then reacted with 1N hydrochloric acid, 150 ml, at about 25° C. for about 12 hours, to yield a dark-red precipitate. The precipitate is filtered off with suction and dried. For further purification, the precipitate is taken up in trichloromethane and worked up by chromatography on aluminium oxide/trichloromethane:

1st fraction: yield 43 mg (26%) (XLV), m.p. 61–63° C., $R_f$ (Al$_2$O$_3$/trichloromethane): 0.82

2nd fraction: yield 91 mg (63%) (XLVI), m.p. 204–205° C., $R_f$ (Al$_2$O$_3$/trichloromethane): 0.42.

Example 2b

N,N'-Bis(1-butylpentyl)perylene-3,4:9,10-bis(dicarboximide)-1-diethylphosphonate (XLVII) and N,N'-bis(1-butylpentyl)pyrrolo[2,3,4,5-hik]perylene-3,4:8,9-bis(dicarboximide) (XLVIII)

(XL), prepared analogously to Example 1a, 300 mg (0.437 mmol) and triethyl phosphite, 10 ml (9.69 g, 58.3 mmol), are reacted under an argon atmosphere at 130° C. for 3 hours. The reaction mixture is then provided with 1N hydrochloric acid, 100 ml, and reacted at about 25° C. for about 12 hours to yield a dark-red precipitate. The precipitate is filtered off with suction and dried. For further purification, the precipitate is taken up in trichloromethane and worked up by chromatography on aluminium oxide (activity level II)/-trichloromethane/1% ethanol:

1st fraction: yield 109 mg (32%) (XLVII), m.p. 122–124° C., $R_f$ (Al$_2$O$_3$/trichloromethane): 0.62.

fraction: yield 160 mg (56%) (XLVIII), m.p.>300° C., $R_f$ (Al$_2$O$_3$, neutral/trichloromethane): 0.24.

Example 3

N,N"-Bis(1-butylpentyl)-N'-methyl-pyrrolo[2,3,4,5-hik]perylene-3,4;8,9-bis(dicarboximide) (XLIX)
Method A (XLVIII), prepared analogously to Example 2b, 100 mg (0.153 mmol), ethanol, 10 ml, and potassium hydroxide powder, 17 mg (0.258 mmol), are reacted with iodomethane, 0.5 ml (8 mmol) at about 25° C. for about 12 hours. The ethanol is then distilled off. The residue of the reaction mixture is taken up in trichloromethane and washed several times with water. The organic solvent phase is then dried with magnesium sulfate and subsequently concentrated to dryness. The residue is taken up in trichloromethane and worked up by chromatography on silica gel/trichloromethane: Yield 93 mg (91%) (XLIX) cherry-red powder.

Method B: (XLVIII), 100 mg (0.153 mmol) and ethanol, 10 ml, are reacted with potassium hydroxide powder, 17.0 mg (0.258 mmol). The resulting violet solution is concentrated, and the residue is taken up in N-methylpyrrolidone and reacted with iodomethane, 0.1 ml (1.6 mmol) ) at 25° C. for 12 hours. The reaction mixture is then poured into water, and sufficient ethanol is added for the N-methylpyrrolidone to dissolve, and stirring is carried out at 25° C. for 12 hours. The ethanol is then distilled off. The residue of the reaction mixture is taken up in trichloromethane and washed several times with water. The organic solvent phase is then dried with magnesium sulfate and subsequently concentrated to dryness. The residue is taken up in trichloromethane and worked up by chromatography on silica gel/trichloromethane. Yield 93 mg (91%) in the form of a cherry-red powder, (XLIX), m.p.>300° C., $R_f$ (silica gel/trichloromethane): 0.61. - $R_f$ (Al$_2$O$_3$/trichloromethane): 0.77.

Example 4

N,N"-Bis(1-hexylheptyl)-N'-benzyl-pyrrolo[2,3,4,5-hik]perylene-3,4:8,9-bis(dicarboximide) (L),
Method A (XLVI), prepared analogously to Example 2a, 100 mg (0.13 mmol), ethanol, 10 ml, and potassium hydroxide powder, 11 mg (0.167 mmol), are reacted with benzyl bromide, 222 mg (1.3 mmol), at 25° C. for 12 hours. The ethanol is then distilled off. The residue of the reaction mixture is taken up in trichloromethane and worked up by chromatography on silica gel/(petroleum ether:trichloromethane) (5:1) and then on silica gel/trichloromethane. Yield 83.0 mg (74%) (L) in the form of a light-red powder.

Method B: N,N"-Bis(1-hexylheptyl)pyrrolo[2,3,4,5-hik]perylene-3,4;8,9-bis(dicarboximide) (XLVI), prepared analogously to Example 2a, 100 mg (0.130 mmol), tetrahydrofuran, 10 ml, and DBU, 30 mg (0.197 mmol), are reacted with benzyl bromide, 222 mg (1.30 mmol), at about 25° C. until the starting material can no longer be detected by thin-layer chromatography. Tetrahydrofuran is then distilled off and working up is carried out analogously to method A. Yield 97 mg (87%) (L), m.p. 134–135° C., $R_f$ (silica gel/trichloromethane): 0.62.

Example 5

N,N"-Bis(1-hexylheptyl)-N'-ethoxycarbonylmethyl-pyrrolo[2,3,4,5-hik]perylene-3,4;89-bis(dicarboximide) (LI)

(XLVI), prepared analogously to Example 2a, 105 mg (0.137 mmol), tetrahydrofuran, 15 ml, and DBU, 31 mg (0.204 mmol), are reacted with bromoacetic acid ethyl ester, 46 mg (0.277 mmol), at about 25° C. until the starting material can no longer be detected by thin-layer chromatography. 2N hydrochloric acid is then added to the batch, followed by as much acetone as required for the excess bromoacetic acid ethyl ester to go into solution. The resulting red precipitate is filtered off, and the filter residue is dried and worked up by chromatography on silica gel/trichloromethane. Yield 95 mg (81%) (LI) in the form of a bright red powder, m.p. 110–111° C., $R_f$ (silica gel/trichloromethane): 0.56.

Example 6a

N,N"-Bis(1-hexylheptyl)-N'-acetyl-pyrrolo[2,3,4,5-hik]perylene-3,4;8,9-bis(dicarboximide) (LII)

(XLVI), prepared analogously to Example 2a, 56 mg (0.07 mmol), dissolved in tetrahydrofuran and DBU, 17 mg (0.11 mmol), are reacted with acetyl chloride, 12 mg (0.15 mmol), at 25° C. until the starting material can no longer be detected by thin-layer chromatography. The reaction mixture is then reacted with water, 50 ml, at 25° C. for 12 hours. The resulting precipitate is filtered off, and the filter residue is isolated and dried and then worked up by chromatography on silica gel/trichloromethane. Yield 43 mg (73%) (LII) in the form of a bright red powder, m.p.>300° C., $R_f$ (silica gel/trichloromethane): 0.62.

Example 6b

N,N"-Bis(1-butylpentyl)-N'-acetyl-pyrrolo[2,3,4.5-hik]perylene-3,4:8,9-bis(dicarboximide) (LIII)

(XLVIII), prepared analogously to Example 2b, 48 mg (0.073 mmol), dissolved in tetrahydrofuran, and DBU, 22 mg (0.145 mmol), are reacted with acetyl chloride, 10 mg (0.128 mmol), at 25° C. until the starting material can no longer be detected by thin-layer chromatography. The reaction mixture is then reacted with water, 50 ml, at 25° C. for 12 hours. The resulting precipitate is filtered off, and the filter residue is isolated and dried and then worked up by chromatography on silica gel/dichloromethane. Yield 35 mg (69%) (LIII) in the form of a bright red powder, m.p.>300° C., $R_f$ (silica gel/trichloromethane): 0.23.

Example 7

N,N"-Bis(1-hexylheptyl)-N'-benzoyl-pyrrolo[2,3,4,5-hik]perylene-3,4;8,9-bis(dicarboximide) (LIV)

(XLVI), prepared analogously to Example 2a, 80.0 mg (0.104 mmol), dissolved in tetrahydrofuran, and DBU, 25 mg (0.164 mmol), are reacted with benzoyl chloride, 44 mg (0.314 mmol), at about 25° C. until the starting material can no longer be detected by thin-layer chromatography. The reaction mixture is then reacted with water, 50 ml, at about 25° C. for about 12 hours. The resulting precipitate is filtered off. The filter residue is isolated and dried and then worked up by chromatography on silica gel/trichloromethane. Yield 84 mg (92%) (LIV) in the form of a bright red powder, m.p. 181–183° C., $R_f$ (silica gel/trichloromethane): 0.51.

Example 8

1-Bromo-N,N'-bis(1-hexylheptyl)perylene-3,4:9,10-bis(dicarboximide) (LV)

N,N'-Bis(1-hexylheptyl)perylene-3,4:9,10-bis(dicarboximide), prepared analogously to Chem. Ber. 1988, 121, 225–230), 200 mg (0.265 mmol), dissolved in chlorobenzene, bromine, 1 ml (39.3 mmol), and anhydrous potassium carbonate, 520 mg (3.77 mmol), are reacted at 60° C. for 24 hours. Chlorobenzene is then distilled off, and the distillation residue is worked up by chromatography on silica gel/trichloromethane. Yield 190 mg (86%) (LV) in the form of a dark-red powder, m.p. 136–138° C. $R_f$ (silica gel/trichloromethane): 0.79.

Example 9

1-Amino-N,N'-bis(1-hexylheptyl)perylene-3,4:9,10-bis(dicarboximide) (LVI)

Method A: (XLI), prepared analogously to Example 1b,100 mg (0.125 mmol), iron, 50 mg (0.893 mmol), and ethanol (or n-butanol or tetrahydrofuran) are reacted under reflux with concentrated hydrochloric acid, 0.5 ml, until (XLI) can no longer be detected by thin-layer chromatography (about 10–30 minutes). The resulting precipitate is then precipitated with water and filtered off. The filter residue is dried and then worked up by chromatography on silica gel/trichloromethane. Yield 78.0 mg (81%) (LVI) in the form of a dark-blue powder Method B: (XLI), prepared analogously to Example 1b, 20 mg (0.025 mmol), dissolved in tetrahydrofuran, triethylamine, 0.200 ml (1.44 mmol), and palladium/carbon, 5 mg (5% by weight), are reacted at boiling temperature for about 30 minutes. Formic acid, 0.040 ml (1.06 mmol) and palladium/carbon, 5 mg (5% by weight) are then added, and the mixture is reacted at boiling temperature for 25 minutes until (XLI) can no longer be detected by thin-layer chromatography. Working up is then carried out analogously to method A. Yield 14 mg (73%) (LVI) in the form of a dark-blue powder, m.p. 93–95° C., $R_f$ (silica gel/trichloromethane): 0.34.

Example 10

1-Dimethylamino-N,N'-bis(1-hexylheptyl)perylene-3,4:9,10-bis(dicarboximide) (LVII), Method A: (LVI), prepared analogously to Example 9, 34 mg (0.044 mmol), dissolved in formic acid, 5 ml, and dimethylformamide, 2 ml, are reacted with formalin solution, 0.5 ml (35% by weight), at 85° C. for 24 hours. Water is then added to the reaction mixture, which is subsequently rendered weakly basic with sodium carbonate. The reaction mixture is filtered and the filter residue is isolated, dried and then worked up by chromatography on silica gel/trichloromethane. Yield: 21 mg (60%) (LVII)

Method B: (LVI), prepared analogously to Example 9, 50 mg (0.065 mmol), dissolved in toluene, potassium hydroxide powder, 15 mg (0.228 mmol) and triethylbenzylammonium chloride, 5 mg (0.022 mmol), are reacted with methyl iodide, 0.04 ml (0.642 mmol), at 25° C. for 12 hours. The reaction mixture is then diluted with the solvent and washed three times with water. The organic solvent phase is separated from the aqueous phase and dried over magnesium sulfate, and the solvent is then removed by distillation. Working up is then carried out by chromatography on silica gel/trichloromethane and then on silica gel/dichloromethane. After elution of the (LVII), there is also obtained as by-product the blueish-green monomethylation product,1-methylamino-N,N'-bis(1-hexylheptyl)perylene-3,4:9,10-bis(dicarboximide), (LVIII). Yield 40 mg (77%) (LVII) in the form of a dark-green solid, m.p. 72–74° C., $R_f$ (silica gel/trichloromethane): 0.63.

Example 11a

1-Amino-N,N'-bis(1-butylpentyl)perylene-3,4:9,10-bis(dicarboximide) (LIX)

(XL), prepared analogously to Example 1a, 100 mg (0.146 mmol), dissolved in tetrahydrofuran, iron, 50 mg (0.893 mmol), and concentrated hydrochloric acid, 0.5 ml, are reacted at boiling temperature until (XL) can no longer be detected by thin-layer chromatography (after about 15 minutes). The reaction mixture is then reacted with water and 2N hydrochloric acid. The resulting precipitate is filtered off. The filter residue comprising (LIX) is isolated and dried.

Example 11b

1-Dimethylamino-N,N'-bis(1-butylpentyl)perylene-3,4:9,10-bis(dicarboximide) (LX)

(LIX), prepared according to Example 11a, is dissolved in dichloromethane, and reacted with potassium hydroxide powder, 30 mg (0.456 mmol), triethylbenzylammonium chloride, 10 mg (0.044 mmol), and methyl iodide, 0.1 ml (1.61mmol), at 25° C. for 12 hours. The reaction mixture is then diluted with dichloromethane and washed three times with water. The dichloromethane phase is separated from the aqueous phase and dried over magnesium sulfate, and then the organic solvent is removed by distillation. Working up is then carried out by chromatography on silica gel/trichloromethane and then on silica gel/dichloromethane. Yield 70 mg (70%) (LX) in the form of a dark-blueish-green product, m.p. 170–172° C., $R_f$ (silica gel/trichloromethane): 0.50.

Example 12a

1-Amino-N-(1-hexylheptyl)perylene-3,4:9,10-tetracarboxylic acid 3,4-anhydride-9,10-imide (LXI) and 12-amino-N-(1-hexylheptyl)perylene-3,4:9,10-tetracarboxylic acid 3,4-anhydride-9.10-imide (LXII)

Method A: A mixture of (XLIII) and (XLIV), prepared according to Example 1d, 100 mg (0.162 mmol), is dissolved in 30 ml of tetrahydrofuran, or in a mixture of trichloromethane and ethanol (in a weight ratio of 3:1/trichloromethane:ethanol), and reacted with iron, 64 mg (1.14 mmol), and concentrated hydrochloric acid, 0.5 ml, at boiling temperature for about 30 minutes. After cooling, the reaction mixture is poured into 2N hydrochloric acid, and acetone is added until a solution is formed (when tetrahydrofuran is used, acetone is not added). The solvent residues are then distilled off. The residue is filtered. The resulting filter residue is dried. (LXI) and (LXII) are obtained in the form of a dark-blue powder, which is reacted further without purification.

Method B: A mixture of (XLIII) and (XLIV), prepared according to Example 1d, 100 mg (0.162 mmol), tetrahydrofuran, 30 ml, triethylamine, 1.3 ml (9.33 mmol), are reacted with palladium/carbon, 15 mg, at boiling temperature for about 30 minutes. Formic acid, 0.26 ml (6.87 mmol) and palladium/carbon, 30 mg, are then added to the reaction mixture, and reaction is carried out at boiling temperature for about 30 minutes until (XLIII) and (XLIV) can no longer be detected by thin-layer chromatography. The reaction mixture is then cooled to about 25° C. and the catalyst is removed by filtration. Further working up is carried out as described above, yielding (LXI) and (LXII) in the form of a dark-blue powder, which is reacted further without purification. M.p. 292–294° C., $R_f$ (silica gel/dichloromethane/2% glacial acetic acid): 0.15–0.40.

Example 12b

1-Dimethylamino-N-(1-hexylheptyl)perylene-3,4-anhydride-9,10-dicarboximide (LXIII) and 12-dimethylamino-N-(1-hexylheptyl)perylene-3,4-anhydride-9,10-dicarboximide (LXIV)

A mixture of (LXI) and (LXII), prepared according to Example 12a, 58 mg (0.099 mmol), dimethylformamide, 7 ml, formic acid, 2 ml, and formalin, 1 ml (37% by weight), are reacted for 24 hours at 105° C. The reaction mixture is then poured into 1N hydrochloric acid. A blueish-green precipitate is produced, which is filtered off. The precipitate is then washed with water. The precipitate is then dried and worked up, with the exclusion of light, by chromatography on silica gel/trichloromethane/glacial acetic acid (5% by weight). Yield 43 mg (71%) (LXIII) and (LXIV), $R_f$ (silica gel/trichloromethane /glacial acetic acid (3% by weight): 0.50; the two isomers are separated by column chromatography on silica gel/trichloromethane/glacial acetic acid (1% by weight);

1st fraction: (LXIII) with $R_f$ (silica gel/trichloromethane/glacial acetic acid (1% by weight)): 0.17;

2nd fraction: (LXIV) with $R_f$ (silica gel/trichloromethane/glacial acetic acid (1% by weight)): 0.11.

Example 13a

N'-Bis(1-butylpentyl)perylo[6,7-cde]-1,2-dithiin-3,4:9,10-bis(dicarboximide) (LXV) and N,N'-bis(1-butylpentyl)perylo[1,12-bcd]-thionhene-3,4:9,10-bis(dicarboximide) (LXVI)

Sulfur, 20 mg (0.63 mmol), is dissolved in N,N'-dimethylformamide, 10 ml, at 80–90° C., and then reacted with 1-nitro-N,N'-bis(1-butylpentyl)perylene-3,4:9,10-bis-(dicarboximide), (XL), prepared according to Example 1a, 100 mg (0.15 mmol), prepared analogously to Example 1a, under an argon atmosphere at 120–130° C. for 10 hours until 1-nitro-N,N'-bis(1-butylpentyl)perylene-3,4:9,10-bis(dicarboximide) can no longer be detected by thin-layer chromatography. The reaction mixture is then poured into a mixture of two parts water and one part 2N hydrochloric acid, about 100 ml. The resulting dark precipitate is filtered off and the filter residue is washed with water. The filter residue is then dried at 70° C. and by chromatography on silica gel/trichloromethane, and then the excess sulfur is removed from fraction 1 on silica gel/petroleum ether (about 2 liters). Elution with trichloromethane is then carried out.

1st fraction: yield 42 mg (42%) (LXV), m.p.>300° C.; $R_f$ (silica gel/trichloromethane): 0.63;

2nd fraction: yield 49 mg (47%) (LXVI) in the form of a bright orange powder, m.p.>300° C., $R_f$ (silica gel/trichloromethane): 0.54.

Example 13b

N,N'-Bis(1-hexylheptyl)perylo[6,7-cde]-1,2-dithiin-3,4:9,10-bis(dicarboximide) (LXVII) and N,N'-bis(1-hexylheptyl)perylo[1,12-bcd]-thiophene-3,4:9,10-bis(dicarboximide) (LXVIII)

Sulfur, 160 mg (4.9 mmol), is dissolved in N-methylpyrrolidone, 12 ml, at 70° C., and reacted with 1-nitro-N,N'-bis(1-hexylheptyl)perylene-3,4:9,10-tetracarboxylic acid 3,4:9,10-bis(dicarboximide), (XLI), 50 mg (0.62 mmol), prepared analogously to Example 1b, under argon at 130° C. for 75 minutes. The reaction mixture is then poured into water, 150 ml. The resulting dark precipitate is filtered off and the filter residue is then washed with water. The residue is then dried at 70° C. and worked up by chromatography on silica gel/trichloromethane, and then the excess sulfur is removed from fraction on silica gel/petroleum ether (about 2 liters). Working up is then carried out on silica gel/trichloromethane.

1st fraction: yield 130 mg (25%) (LXVII), m.p. 158–160° C., $R_f$ (silica gel/trichloromethane): 0.72;

2nd fraction: yield 295 mg (60%) (LXVIII) in the form of a bright orange powder, m.p. 263–265° C., $R_f$ (silica gel/trichloromethane): 0.67.

Example 13c

Bis(2,5-di-tert-butylphenyl)-perylo[6.7-cde]-1.2-dithiin-3,4:9,10-bis(dicarboximide) (LXIX) and N,N'-bis(2,5-di-tert-butylphenyl)-perylo[1,12-bcd]thiophene-3,4:9,10-bis-(dicarboxidmide) (LXX)

Sulfur, 24.0 mg (0.750 mmol) is dissolved in N,N'-dimethylformamide, 10 ml, at 90° C. and reacted 1-nitro- N,N'-bis(2,5-di-tert-butylphenyl)perylene-3,4:9,10-bis(dicarboximide), (XLII), (prepared as in Example 1c) 100 mg (0.123 mmol), under argon at 120° C. for 17 hours until 1-nitro-N,N'-bis(2,5-di-tert-butylphenyl)perylene-3,4:9,10-(dicarboximide) can no longer be detected by thin-layer chromatography. The reaction mixture is then poured into a mixture of two parts water and one part 2N hydrochloric acid, about 100 ml. The resulting dark precipitate is filtered off, and then the filter residue is washed with water. The residue is then dried at 70° C. and worked up by chromatography.

1st fraction: yield 56 mg (55%) (LXIX), m.p.>300° C., $R_f$ (silica gel, trichloromethane): 0.36;

2nd fraction: yield 29 mg (30%) (LXX) in the form of a bright orange powder, m.p.>300° C.; $R_f$ (silica gel/trichloromethane): 0.32.

Example 14a

N,N'-Bis(1-hexylheptyl)benzoperylene-1',2':3,4:9, 10-hexacarboxylic acid 1',2'-anhydride-3,4:9,10-bis(dicarboximide) (LXXI)

N,N'-Bis(1-hexylheptyl)perylene-3,4:9,10-bis(dicarboximide), prepared analogously to Chem. Ber.—121, 225–230, 1.50 g, (1.99 mmol), molten maleic acid anhydride (at 95° C.) and a few milliliters of acetone, are heated with chloranil, 970 mg (3.98 mmol) at 125° C. for 4 days. The reaction mixture is then cooled to about 30–40° C., poured into a mixture of acetone and 2N hydrochloric acid, 250 ml, and reacted at 25° C. for 12 hours. The reaction mixture is then filtered, and the filter residue is washed several times with water and then dried. The dried filter residue is then dissolved in trichloromethane and worked up by chromatography on silica gel/trichloromethane. The first fraction eluted is the excess chloranil and N,N'-bis(1-hexylheptyl)perylene-3,4:9,10-bis(dicarboximide). Chromatography is then continued with a mixture of trichloromethane and glacial acetic acid (1–5% by weight) and (LXXI) is eluted. Yield 1.20 g (71%) (LXXI) in the form of a dark-yellow powder, m.p.>200° C. (decomp.), $R_f$ (silica gel/trichloromethane/glacial acetic acid 10:1): 0.81.

Example 14b

N,N'-Bis(1-butylpentyl)benzoperylene-1',2':3,4:9,10-hexacarboxylic acid 1',2'-anhydride-3,4:9,10-bis(dicarboximide) (LXXII):

N,N'-Bis(1-butylpentyl)perylene-3,4:9,10-bis(dicarboximide) (prepared as above), 500 mg (0.779 mmol), molten maleic acid anhydride (at 95° C.) and a few milliliters of acetone are reacted with chloranil, 380 mg (1.56 mmol), and worked up as in Example 14a. Yield 450 mg (77%) (LXXII) in the form of a bright orange powder, m.p.>300° C., $R_f$ (silica gel/trichloromethane): 0.00–0.12.

Example 14c

N,N'-Bis(2,5-di-tert-butylphenyl)benzoperylene-1', 2':3,4:9,10-hexacarboxatic acid 1',2'-anhydride-3, 4:9,10-bis(dicarboximide) (LXXIII)

N,N'-Bis(2,5-di-tert-butylphenyl)perylene-3,4:9,10-bis(dicarboximide) (prepared as above), 300 mg (at 95° C.) and a few milliliters of acetone are reacted with chloranil, 240 mg (0.984 mmol), as in Example 14a, and worked up. The reaction mixture is purified by chromatography on silica gel/trichloromethane/ethanol (10% by weight) and then on silica gel/trichloromethane/glacial acetic acid (10% by weight). Yield 230 mg (67%) (LXXIII) in the form of a dark-yellow powder, m.p.>300° C., $R_f$ (silica gel/trichloromethane/ethanol (10% by weight)): 0.00–0.16.

Example 15a

N,N'-Bis(1-hexylheptyl)benzoperylene-1',2':3,4:9, 10-hexacarboxylic acid 1',2-bisethoxycarbonyl-3, 4:9,10-bis(dicarboximide) (LXXIV)

(LXXI), 110 mg (0.127 mmol), prepared analogously to Example 14a, dissolved in tetrahydrofuran, and DBU, 60 mg (0.395 mmol), are reacted with ethyl iodide, 100 mg (0.641 mmol), at 25° C. for 12 hours. The reaction mixture is then poured into water, 150 ml, then rendered weakly acidic with 2N hydrochloric acid and reacted at 25° C. for 12 hours. The reaction mixture is filtered, and the filter residue is dried and then worked up by chromatography on silica gel/trichloromethane. Yield 100 mg (85%) (LXXIV) in the form of a bright orange powder, m.p.: 273–275° C., $R_f$ (silica gel/trichloromethane): 0.65.

Example 15b

N,N'-Bis(2,5-di-tert-butylphenyl)benzoperylene-1', 2':3,4:9,10-hexacarboxylic acid 1',2'-bisethoxycarbonyl-3,4:9,10-bis(dicarboximide) (LXXV)

(LXXIII), 50 mg (0.060 mmol), prepared analogously to Example 14c, dissolved in tetrahydrofuran, and DBU, 35 mg (0.23 mmol), are reacted with ethyl iodide, 45 mg (0.29 mmol) as in Example 15a and worked up. Purification by chromatography is carried out on silica gel/trichloromethane/ethanol (3% by weight), yield: 41 mg (78%) (LXXV) in the form of an egg-yolk-yellow powder, m.p.>300° C., $R_f$ (silica gel/trichloromethane): 0.24.

Example 16

N,N''-Bis(1-hexylheptyl)-N'-cyclohexyl-benzoperylene-1',2':3,4:9,10-hexacarboxylic acid 1', 2':3,4:9,10-tris(dicarboximide) (LXXVI)

(LXXI), 100 mg (0.118 mmol), prepared analogously to Example 14a, cyclohexylamine, 114 mg (1.15 mmol), and quinoline, 10 ml, are reacted at 160° C. for 6 hours. The reaction mixture is then poured into 2N hydrochloric acid, 100 ml, and stirred for a few hours at about 25° C. The resulting precipitate is then filtered off and the filter residue is dried and worked up by chromatography on silica gel/trichloromethane. Yield: 71 mg (66%) (LXXVI) in the form of an orange-yellow powder, m.p.>300° C., $R_f$ (silica gel/trichloromethane): 0.63.

Example 17

N,N''-Bis(1-hexylheptyl)-N'-2,5-di-tert-butylphenylbenzoperylene-1',2':3,4:9,10-hexacarboxylic acid 1',2':3,4:9,10-tris(dicarboximide) (LXXVII)

(LXXI), prepared analogously to Example 14a, 60.0 mg (0.0710 mmol), 2,5-di-tert-butylaniline, 100 mg (0.488 mmol), and DCC, 75 mg (0.364 mmol), are boiled with trifluoroacetic acid (1drop) at boiling temperature for about 24 hours. The reaction mixture is then diluted with trichloromethane, and subsequently washed several times with water. The organic solvent phase is separated from the aqueous phase, concentrated in vacuo and purified by chromatography on silica gel/trichloromethane, and then aluminium oxide neutral/petroleum ether/3% trichloromethane). Yield: 50 mg (70%; yield 50% after 4 days' reaction time when only DCC or only trifluoroacetic acid is used) in the form of a bright-yellow solid, m.p.: 285–287° C., $R_f$ (silica gel/trichloromethane): 0.66.

Example 18a

N,N'-Bis(1-hexylheptyl)benzoperylene-3,4:9,10-tetracarboxylic acid 3,4:9,10-bis(dicarboximide) (LXXVIII)

(LXXI), prepared analogously to Example 14a, 50 mg (0.060 mmol) and copper(I) oxide, 40 mg (0.28 mmol), in quinoline are reacted under an argon atmosphere at 180° C. for 4 hours. The reaction mixture is then cooled to about 25–30° C., poured into 2N hydrochloric acid, and treated at about 25–30° C. for 12 hours. The resulting precipitate is filtered off with suction, dried and worked up by chromatography on silica gel/trichloromethane. Yield: 16 mg (36%) (LXXVIII) in the form of a yellow- to orange-coloured powder, m.p. 289–291° C., $R_f$ (silica gel/trichloromethane): 0.82.

Example 18b

N,N'-Bis(1-hexylheptyl)benzoperylene-3,4:9,10-tetracarboxylic acid 3,4:9,10-bis(dicarboximide)

(LXXVIII): (LXXI), prepared analogously to Example 14a, 50 mg (0.060 mmol), and copper powder, 40 mg (0.64 mmol) in 3-picoline are reacted under an argon atmosphere at boiling temperature for 3 days. The reaction mixture is then cooled to about 25–30° C., poured into 2N hydrochloric acid, and treated at 25–30° C. for 12 hours. The resulting precipitate is filtered off with suction, dried and worked up by chromatography on silica gel/trichloromethane. Yield: 21.3 mg (48%) (LXXVIII) in the form of a yellow to orange powder, m.p.: 289–291° C., $R_f$ (silica gel/trichloromethane): 0.82.

Example 19a

N,N'-Bis(1-hexylheptyl)-2-phenyl-benzo[4.10]anthrar[1,9,8cdef][1,2,4]triazolo [1,2-a]cinnoline-1,3-dione-5,6:11,12-bis(dicarboximide) (LXXIX)

N,N'-Bis(1-hexylheptyl)-perylene-3,4:9,10-tetracarboxylic acid 3,4:9,10-bis(dicarboximide) (prepared as above), 100 mg, (0.133 mmol), 4-phenyl-1,2,4-triazoline-3,5-dione, 180 mg (1.03 mmol) and chloranil, 32.5 mg (0.133 mmol), are reacted in dried toluene for 24 hours at boiling temperature. Toluene is then removed from the reaction mixture by distillation, and the residue is worked up by chromatography on silica gel/trichloromethane and then on silica gel/dichloromethane. Yield: 32 mg (25%) (LXXIX) in the form of a green solid, m.p.>300° C., $R_f$ (silica gel/trichloromethane): 0.32, $R_f$ (silica gel/dichloromethane): 0.56.

Example 19b

N,N'-Bis(1-hexylheptyl)-2-phenyl-benzo[4,10]anthra[1,9,8-cdef][1,2,4]triazolo[1,2-a]cinnoline-1,3-dione-5,6:11,12-bis(dicarboximide) (LXXIX) or (XVI)

N,N'-Bis(1-hexylheptyl)perylene-3,4:9,10-tetracarboxylic acid 3,4:9,10-bis(dicarboximide) (prepared as above), 500 mg (0.665 mmol), and para-chloranil, 163 mg (0.665 mmol), in dried toluene are reacted with 4-phenyl-1,2,4-triazoline-3,5-dione, in 6 weight-equivalent portions each of 139 mg (1.11 mmol) at time intervals of about 2 hours at boiling temperature, and then heated at boiling temperature for a further 12 hours. Toluene is then removed from the reaction mixture by distillation and the residue is worked up by chromatography on silica gel/trichloromethane and then on silica gel/dichloromethane. Yield.: 252 mg (41%) (LXXIX); or in the form of a blue compound (XVI), wherein $R^1$ and $R^2$ are N-1-hexylheptyl, and $R^4$ is phenyl, $R_f$=0.16 (CHCl$_3$).

Example 20

11,12-Diaza-11,12-dihydrobenzo[ghi]-perylene-2,3,8,9,11,12-hexacarboxylic acid 2,3:8,9-bis(1-hexylheptylimide)-11,12-diisopropyl ester (LXXX) 11,12-diazabenzo [ghi]perylene-2,3,8,9-tetracarboxylic acid 2,3:8,9-bis(1-hexylheptylimide) (LXXXI)

N,N'-Bis(1-hexylheptyl)perylene-3,4:9,10-tetracarboxylic acid 3,4:9,10-bis(dicarboximide) (prepared as above), 100 mg (0.133 mmol), dissolved in 5 ml of toluene, 5.05 g (25 mmol) of diisopropyl azodicarboxylate and 64 m (0.26 mmol) of para-chloranil are reacted at 140° C. for a week. Working up is then carried out by chromatography on silica gel/trichloromethane. (LXXX) and (LXXXI) are identified in the mass spectrum by the mass unit: (LXXX) of 955 u, and (LXXXI) of 781 u.

Example 21

11,12-Diaza-11,12-dihydrocoronene-2,3,5,6,8,9,11,12-octacarboxylic acid 5,6-anhydride-2,3:8,9-bis (1-hexylheptylimide)-11,12-phenylimide (LXXXII)

(LXXIX), prepared as in Example 19a, 250 mg (0.27 mmol), molten maleic acid anhydride, 10 g (102 mmol), and para-chloranil, 132 mg (0.54 mmol), are reacted for four weeks at 125° C. with a small amount of trichloromethane for flushing back evaporated maleic acid anhydride. Working up is carried out by column chromatography on silica gel with dichloromethane to remove the starting materials, and then elution is carried out with dichloromethane/5% glacial acetic acid. Yield: 57%, $R_f$ value: 0.0–0.6 (CH$_2$Cl$_2$).

Example 22

0.5 g (0.66 mmol) of N,N'-bis(1-hexylheptyl)perylene-3,4:9,10-bis(dicarboximide) and 0.32 g (1.32 mmol) of p-chloranil are added to 10 g of molten N-phenylmaleimide. A small amount of chloroform is added to the resulting mixture and heating is carried out for three days at 120° C. A small amount of chloroform is then added and the product is precipitated with a large amount of methanol. Filtration yields 575 mg (94%) of the desired product (formula IXb, $R^4$=phenyl, $R^1$=$R^2$=1-hexylheptyl), $R_f$ value (CHCl$_3$)=0.8.

Example 23

N,N'-Bis(1-hexylheptyl)benzo[ghi]perylene-2,3,8,9,11,12-hexacarboxylic acid 2,3;8,9-bis(dicarboximide)-11,12-dicarboximide (IXa)

1.00 g (1.17 mmol) of N,N'-bis(1-hexylheptyl)benzo[ghi]perylene-2,3,8,9,11,12-hexacarboxylic acid 2,3;8,9-bis(dicarboximide)-11,12-anhydride is mixed with 6 g of imidazole. 4.57 g (47.16 mmol) of finely pulverised amidosulfuric acid are then added, and the batch is stirred for four hours under an argon atmosphere in an oil bath at an oil-bath temperature of 160° C. After a few minutes, perceptible reaction commences, the batch quite recognisably changing from dark yellow to brown. After the reaction is complete, the batch is left to cool slowly, and is flushed out of the flask with 400 ml of 2N hydrochloric acid and stirred further for about one hour at room temperature. The precipitate is filtered off with suction, then washed with a further 200 ml of twice-distilled water and dried overnight at 120° C. in a drying cabinet. The resulting crude product is dissolved in a small amount of chloroform, applied to a silica gel column and then chromatographed with the eluant mixture chloroform/acetone (15:1). In that process, after separation of a yellowish-green-fluorescent first running, the product is obtained in the form of broad, reddish-yellow bands. For further purification, the dye is chromatographed again over a neutral aluminium oxide with the eluant mixture chloroform/acetone (15:1). The resulting solution is concentrated and, after cooling, the dye is precipitated slowly with methanol. The resulting precipitate is filtered off and dried at 80° C. in an atmosphere under reduced pressure, yielding 0.83 (84%) of a light-yellow bright powder having a melting point of>260° C. (decomposition). $R_f$ (chloroform/ acetone 15:1): 0.74. Fluorescence (chloroform, corrected) $\lambda_{max.}$ (rel. intensity)=481nm (0.99), 508 (1.00), 550 (0.56).

Fluorescence quantum yield (chloroform): $\phi$=49%, based on perylene-3,4:9,10-tetracarboxylic acid tetramethyl ester (100%) as standard.

What is claimed:

1. A nucleus-extended perylenebisimide of general formula (I)

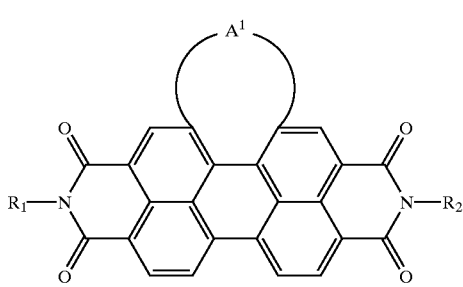

(I)

wherein $R^1$ and $R^2$ are each independently of the other secondary alkyl radical of the formula 1-($C_1$–$C_9$alkyl) –$C_2$–$C_{10}$alkyl, $C_1$–$C_{24}$cycloalkyl, or $C_6$–$C_{10}$aryl, and $A^1$ is —S—, —S—S—, -CH=CH—, $R^3$OOC—C(—)=C(—)—COOR$^3$, —N=N— or —N($R^4$)—, or a linkage selected from the group consisting of the organic radicals of formulae (III), (IV), (V), (VI) and (VII)

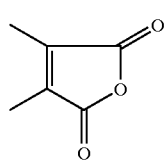

(III)

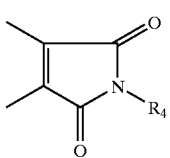

(IV)

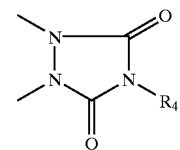

(V)

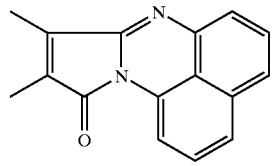

(VI)

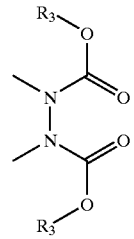

(VII)

wherein $R^3$ is hydrogen, $C_1$–$C_{24}$ alkyl or $C_1$–$C_{24}$cycloalkyl, and $R^4$ is unsubstituted or substituted $C_1$–$C_{24}$alkyl, $C_1$–$C_{24}$cycloalkyl, phenyl, benzyl, –CO–$C_1$–$C_4$alkyl, –CO–$C_6$H$_5$ or $C_1$–$C_4$alkylcarboxylic acid ($C_1$–$C_4$alkyl) ester.

with the proviso that when Al is —s—, then either $R_1$ or $R_2$ is not a phenyl group.

2. A process for the preparation of perylenebisimides (I) according to claim 1, wherein $A^1$ is $A^4$, wherein $A^4$ is a linkage selected from the group consisting of the organic radicals of formulae (III), (IV), (V), (VII) and —N=N—, by Diels-Alder reaction of a diene with a dienophile at elevated temperaure, wherein therein there are reacted, as diene, a perylenebisimide of formula (XXI)

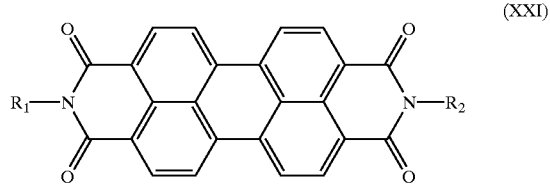

(XXI)

and, as dienophile, a compound selected from the group consisting of the compounds of formulae (XXII), (XXIII) and (XXIV)

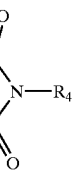

XXII

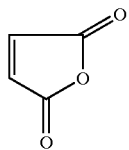
(XXIIa)

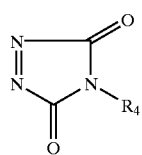
(XXIII)

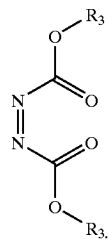
(XXIV)

3. A method for coloring high molecular weight organic material comprising incorporating at least one perylene according claim 1 into said high molecular organic material, wherein said high molecular weight organic material is a polymeric material.

4. A method according to claim 3 wherein the high molecular weight organic material is selected from the group consisting of polyvinyl chloride, cellulose acetate, polycarbonate, polyamide, polyurethane, polyimide, polybenzimidazole, melamine resin, silicone, polyester, polyether, polystyrene, polymethyl methacrylate, polyethylene, polypropylene, polyvinyl acetate, polyacrylonitrile, polybutadiene, polychlorobutadiene, polyisoprene, and copolymers and mixtures thereof.

5. A method for preparing a dye composition comprising incorporating at least one perylene according claim 1 into a homogenous solution suitable for use as a dye.

6. A method for preparing a coating composition comprising incorporating at least one perylene according to claim 1 into a homogenous solution suitable for use as a coating for a substrate.

7. A method according to claim 5, wherein the coating composition is selected from the group consisting of a paint product, lacquer, paper dyes or printing ink.

* * * * *